US012790404B2

(12) United States Patent
Matosevic et al.

(10) Patent No.: US 12,790,404 B2
(45) Date of Patent: *Nov. 10, 2026

(54) ENGINEERED NATURAL KILLER CELLS REDIRECTED TOWARD PURINERGIC SIGNALING, CONSTRUCTS THEREOF, AND METHODS FOR USING THE SAME

(71) Applicant: Purdue Research Foundation, West Lafayette, IN (US)

(72) Inventors: Sandro Matosevic, Lafayette, IN (US); Andrea Marie Chambers, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1304 days.

This patent is subject to a terminal disclaimer.

(21) Appl. No.: 17/606,412

(22) PCT Filed: Apr. 27, 2020

(86) PCT No.: PCT/US2020/030100

§ 371 (c)(1),
(2) Date: Oct. 25, 2021

(87) PCT Pub. No.: WO2020/220027

PCT Pub. Date: Oct. 29, 2020

(65) Prior Publication Data

US 2022/0193138 A1 Jun. 23, 2022

Related U.S. Application Data

(60) Provisional application No. 62/838,742, filed on Apr. 25, 2019.

(51) Int. Cl.

| | |
|---|---|
| ***C07K 16/28*** | (2006.01) |
| ***A61K 38/00*** | (2006.01) |
| ***A61K 39/00*** | (2006.01) |
| ***A61K 40/15*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 14/735*** | (2006.01) |
| ***C12N 5/0783*** | (2010.01) |

(52) U.S. Cl.

CPC .......... *C07K 16/2896* (2013.01); *A61K 40/15* (2025.01); *A61K 40/31* (2025.01); *A61K 40/4224* (2025.01); *A61P 35/00* (2018.01); *C07K 14/70535* (2013.01); *C12N 5/0646* (2013.01); *A61K 38/00* (2013.01); *A61K 2039/505* (2013.01); *A61K 2239/31* (2023.05); *A61K 2239/38* (2023.05); *A61K 2239/55* (2023.05); *C07K 2317/53* (2013.01); *C07K 2317/622* (2013.01); *C07K 2317/76* (2013.01); *C07K 2319/03* (2013.01); *C07K 2319/30* (2013.01); *C12N 2506/45* (2013.01); *C12N 2510/00* (2013.01)

(58) Field of Classification Search

None

See application file for complete search history.

(56) References Cited

U.S. PATENT DOCUMENTS

2018/0161371 A1 6/2018 O'Dwyer

FOREIGN PATENT DOCUMENTS

| | | | | |
|---|---|---|---|---|
| EP | 3311832 | A1 * | 4/2018 | ............. A61K 35/17 |
| WO | 2017025323 | A1 | 2/2017 | |
| WO | 2017149515 | A1 | 9/2017 | |
| WO | WO-2018002358 | A1 * | 1/2018 | ............. A61K 35/17 |
| WO | 2018144535 | A1 | 8/2018 | |
| WO | 2018177966 | A1 | 10/2018 | |
| WO | 2018204427 | A1 | 11/2018 | |

OTHER PUBLICATIONS

Li et al. "Human iPSC-Derived Natural Killer Cells Engineered with Chimeric Antigen Receptors Enhance Anti-tumor Activity", Cell Stem Cell. Aug. 2, 2018;23(2):181-192.e5 (Year: 2018).*
International Searching Authority, International Search Report, PCT Application No. PCT/US2020/030100, dated Aug. 12, 2020.
International Searching Authority, Written Opinion of the International Searching Authority, PCT Application No. PCT/US2020/030100, dated Aug. 12, 2020.
European Patent Office, European Search Report, EPO Application No. 20794720.1, dated Apr. 14, 2023, DE.
Allard et al., Targeting the CD73-adenosine axis in immuno-oncology, Immunology Letters 205: 31-39 (May 24, 2018), Elsevier, NL.
Zhang et al., Prospects for chimeric antigen receptor-modified T cell therapy for solid tumors, Molecular Cancer 17(1) (Jan. 12, 2018), BioMed Central, Springer Nature, GB.

* cited by examiner

*Primary Examiner* — Peter Johansen
(74) *Attorney, Agent, or Firm* — Reichel Stohry Dean LLP; Natalie J. Dean

(57) ABSTRACT

Polynucleotide constructs and engineered natural killer (NK) cells expressing such constructs are provided for the treatment of cancer and other adenosine-overexpressing disease states. The constructs are a fusion of at least an antigen binding domain specific to an adenosine producing (or adenosine-intermediary producing) cell surface protein and a receptor for promoting cytotoxic or cytolytic activity of the NK cell upon activation, where activation occurs upon the antigen binding domain binding its target cell. Pharmaceutical compositions of the engineered NK cells are also provided, as well as methods of treating an adenosine overexpressing cancer using such pharmaceutical compositions.

13 Claims, 10 Drawing Sheets

Specification includes a Sequence Listing.

ENGINEERED NATURAL KILLER CELLS REDIRECTED TOWARD PURINERGIC SIGNALING, CONSTRUCTS THEREOF, AND METHODS FOR USING THE SAME

PRIORITY

This application is related to and claims priority benefit of, and is a 35 U.S.C. 371 national stage application of International Patent Application No. PCT/US2020/030100, filed Apr. 27, 2020, which is related to and claims the priority benefit of U.S. Provisional Patent Application Ser. No. 62/838,742 to Matosevic et al. filed Apr. 25, 2019. The contents of the aforementioned applications are hereby incorporated by reference in their entireties into this disclosure.

FIELD

This disclosure relates to targeting adenosinergic signaling in conjunction with NK-based immunotherapy. Particularly, modulation of adenosinergic pathway through CD73 blockade is used to enhance immunotherapy of $CD73^+$ solid tumors with chimeric antigen receptor (CAR)-NK cells in vivo.

BACKGROUND

As important effectors of innate immunity, natural killer (NK) cells are unique and play pivotal functions in cancer immune surveillance. Unlike T cells that only detect major histocompatibility complex (MHC) presented on infected cell surfaces, NK cell function is driven by a balance of activating and inhibitory receptors through which they interact with pathogens and recognize MHC class I molecules on cancer cells. NK cells can eliminate a variety of abnormal or stressed cells without prior sensitization and even preferentially kill stem-like cells or cancer stem cells. Upon forming immune synapses with target cells, NK cells release cytokines that induce cell lysis.

However, cancers employ various tactics to delay, alter, or even stop immune suppressive pathways to prevent the malignant cells from being recognized as dangerous or foreign. These mechanisms prevent the cancer from being eliminated by the immune system, leading to failures in the control of tumor growth and allowing for disease to progress from a very early stage to a lethal state. The anti-tumor response of NK cells also faces many limitations.

Primarily, the tumor microenvironment itself remains a major barrier contributing to the dysregulation of NK cells and, thus, suppression of NK cell anti-tumor immunity. Solid malignancies are commonly characterized by severe tumor hypoxia which occurs as a direct consequence of elevated cancer cell proliferation, altered metabolism, and impaired oxygen and nutrient transport due to abnormal tumor vasculature. Solid tumors are particularly prone to hypoxic regions due to inadequate blood flow and disrupted supply of oxygen. As a result, low tumor oxygenation constitutes a major problem for solid tumor patients.

Pathophysiologic conditions of hypoxia and ischemia, such as those found in solid tumors, drive significant metabolic changes in adenine nucleotides such as adenosine 5'-triphosphate (ATP) and adenosine diphosphate (ADP). Under normal physiological conditions, ATP is localized in the intracellular compartment where concentrations vary between about 1 to 10 mM and is only present at negligible levels (10-100 nM) in the extracellular environment. However, levels of extracellular ATP (and thus adenosine) rise significantly in response to hypoxia, ischemia and the setting of malignancy, defining features of the tumor environment. For example, intratumoral extracellular ATP concentrations can be up to 1,000 times higher than those in normal tissues of the same origin cell.

Extracellular ATP provokes inflammation by "purinergic signals" and plays a significant role in promoting anti-tumor responses. However, where cancer cells release ATP in large amounts, the onset of immunosuppressive adenosine signaling is triggered that blocks the cytotoxic activity of NK cells, for example, by binding to adenosine $A_{2A}$ receptors expressed on NK cells. Adenosinergic signaling impairs the maturation of NK cells, the accumulation of cytotoxic $CD56^{dim}$ cells at tumor sites, the expression of activating NK receptors, and NK effector function; thus, high concentrations of extracellular adenosine in a solid tumor microenvironment interferes with these functions.

Furthermore, changes in NK cell-activating receptors and their ligands in tumors may lead a decreased therapeutic response, resulting in impaired anti-tumor immunity and tumor progression. For example, ectonucleoside triphosphate diphosphohydrolase-1 (CD39) and ecto-5'-nucleotidase (CD73) are surface enzymes expressed on multiple cells (including both infiltrating immune cells and tumor cells) that mediate the gradual hydrolysis of ATP and ADP to anti-inflammatory adenosine. Immune suppression mediated by adenosinergic pathways is very important for maintaining immune system homeostasis; however, this pathway can be hijacked particularly in solid tumor cancers.

Elevated CD39 and CD73 expression has been described in various cancer types and is associated with worse overall survival in solid tumor patients. These ectoenzymes have been shown to interfere with trafficking and activities of NK cells into solid tumor sites via heterologous desensitization of chemokine receptors and reduced proinflammatory cytokines, further promoting cancer development. As a result, adenosinergic signaling through CD39 and CD73 is a negative feedback loop that prevents excessive inflammation and tissue damage thus inhibiting systemic anti-tumor response.

Conventional techniques to effect adenosinergic signaling through a blockade are limited to anti-CD73 treatment and resulted in tumor inhibition that relied heavily on recruitment of NK cells and the presence of NK-produced interferon-γ (IFN-γ) and perforin. Indeed, to date, the blockade has been limited to CD73, only attempted with antibodies, and does not in any way address downregulation of NK activating receptors. Systemic administration of CD73 blockade antibodies risk elevated toxicities and off-target effects, while the efficacy of these antibodies is limited by the presence of clones that act on CD73 through clustering and internalization with no measurable effect on enzymatic activity. Further, while engineering NK cells with chimeric antigen receptor (CAR)-expressing has been attempted, to date, it has only been attempted with the NK92 cell line, which consists of aneuploid cells that must be irradiated before being administered to patients. Irradiation limits the survival and proliferations of NK cells, which are two key criteria known to correlate with improved efficacy of the NK cell-based immunotherapy. Therefore, a need exists to develop a commercially viable and safe method for direct engagement of effector function NK cells to $CD73^+$ solid tumor cells despite such tumor mediated inhibitory effect to NK cells.

SUMMARY

Inventive polynucleotide constructs are provided. In at least one exemplary embodiment, such a polynucleotide construct comprises a first sequence operably linked to a second sequence, where the first sequence encodes at least an antigen binding domain or fragment thereof that is specific for an adenosine-producing or an adenosine-intermediary-producing cell surface protein of a target cell. The second sequence encodes one or more stimulatory or costimulatory domains of a natural killer (NK) cell for promoting cytotoxic or cytolytic activity upon activation. For example, and without limitation, the one or more stimulatory or costimulatory domains may comprise a Fcγ-signal molecule. In at least one embodiment, the one or more stimulatory or costimulatory domains are activated upon the antigen binding domain binding the target cell.

In certain embodiments of the polynucleotide construct of the present disclosure, the antigen binding domain or fragment thereof encoded by the first sequence may be specific for CD38, CD39, CD73, or CD157. Additionally or alternatively, the target cells may be a T regulatory cell, a cancer cell, a solid tumor cell, or a malignant cell in a tumor microenvironment.

The one or more stimulatory or costimulatory domains encoded by the second sequence of the construct may comprise a transmembrane domain and an intracellular domain. Optionally, the one or more stimulatory or costimulatory domains may additionally comprise at least a portion of an extracellular domain. For example, and without limitation, the at least a portion of an extracellular domain may comprise a truncated extracellular domain of FcγRIIIA comprising at or between 189-208 amino acids (inclusive of the end values of the range). In certain other embodiments, the second sequence further comprises a nucleotide sequence that encodes CD3ζ.

In at least one exemplary embodiment, the one or more stimulatory or costimulatory domains are selected from a group consisting of FcγRIIIA, CD28, 4-1BB, OX40, FasL, TRAIL, NKG2D, DAP10, DAP12, NKp46, NKp44, NKp30, LFA-1, CD244, CD137, CD3ζ and a NKG2D-DAP10 receptor complex. Still other embodiments comprise one or more stimulatory or costimulatory domains comprising a transmembrane domain of FcγRIIIA, an intracellular domain of FcγRIIIA, and an extracellular domain of FcγRIIIA (truncated or otherwise).

The novel polynucleotide constructs of the present disclosure may optionally comprise a third sequence that encodes a hinge domain, with the third sequence operably linked to and positioned between the first and second sequence. Such a hinge domain may comprise a linker or spacer (as desired). Furthermore, the first sequence that encodes the antigen binding domain may additionally encode a single chain antibody fragment.

In at least one embodiment, for example, the first sequence is SEQ ID NO: 7 and the second sequence is SEQ ID NO. 8. In yet another exemplary embodiment, the polypeptide construct is SEQ ID NO: 9.

Engineered cells or cell lines are also provided that express the inventive polynucleotide constructs of the present disclosure. In at least one embodiment, an engineered cell or cell line is provided that expresses a polynucleotide construct that encodes at least an antigen binding domain or a fragment thereof and one or more stimulatory or costimulatory domains of a natural killer (NK) cell. There, the antigen binding domain is specific for an adenosine-producing or adenosine-intermediary-producing cell surface protein of a target cell and the one or more stimulatory or costimulatory domains promote(s) cytotoxic or cytolytic activity of the engineered cell or cell line upon activation. Each engineered cell may express the antigen binding domain at a surface of the engineered cell.

In certain embodiments, the engineered cell or cell line may comprise an NK cell or a stem cell. For example, in at least one embodiment, the engineered cell is a NK cell and stem-cell derived. Further the claimed cells or cell lines may be a human cell or cell line.

The one or more stimulatory or costimulatory domains of the engineered cells/cell line may comprise a Fc-signal molecule. For example, and without limitation, the Fc-signal molecule of the one or more stimulatory or costimulatory domains may comprise at least a transmembrane domain of FcγRIIIA and an intracellular domain of FcγRIIIA. In yet another embodiment, the one or more stimulatory or costimulatory domains are selected from a group consisting of FcγRIIIA, CD28, 4-1BB, OX40, FasL, DAP10, DAP12, NKp46, NKp44, NKp30, CD224, CD137, CD3ζ and a NKG2D-DAP10 receptor complex. Still further, the one or more stimulatory or costimulatory domains may comprise a transmembrane domain of FcγRIIIA, an intracellular domain of FcγRIIIA, and at least a partial extracellular domain of FcγRIIIA.

Pharmaceutical compositions are also provided that leverage the inventive concepts of the present disclosure. In at least one embodiment, a pharmaceutical composition is provided that comprises a population of the engineered cells described herein. For example, may comprise a first population of engineered cells that express at least one construct of the present disclosure such that the cells comprise the antigen binding domain and the one or more stimulatory or costimulatory domains that are activated upon the antigen binding domain binding the target cell. Such pharmaceutical compositions may additionally include a pharmaceutically acceptable carrier.

Methods of treating a subject having an adenosine overexpressing disease state are also provided. In at least one embodiment, such a method comprises the steps of administering, or having administered, to a subject a therapeutically effective amount of a pharmaceutical composition comprising a first population of engineered cells. Administration may occur, for example, via intravenous administration, intratumorally, parenterally, or infusion techniques.

There, such engineered cells express a first polynucleotide construct encoding 1) at least an antigen binding domain or a fragment thereof, and 2) one or more stimulatory or costimulatory domains of a NK cell. In at least one exemplary embodiment, the antigen binding domain is specific for an adenosine-producing or adenosine-intermediary-producing cell surface protein of a target cell and the one or more stimulatory or costimulatory domains promote cytotoxic or cytolytic activity of an engineered cell of the first population upon the antigen binding domain of such engineered cell binding the target cell. Optionally, where the engineered cells comprise NK cells, the method may further comprise expanding the number of engineered cells in the first population.

Similarly, the antigen binding domain or fragment thereof of the engineered cells/cell line may be specific for CD39 or CD73. Additionally or alternatively, the target cell may be a T regulatory cell, a cancer cell, or a malignant cell in a tumor microenvironment.

In yet other embodiments, the pharmaceutical composition may further comprise a second population of engineered cells that are engineered to be specific to a second ligand. For example, and without limitation, the first population of engineered cells may express the first polynucleotide construct that encodes at least an antigen binding domain or fragment thereof that is specific for CD73, whereas the first population of engineered cells expresses a second polynucleotide construct that encodes at least an antigen binding domain or fragment thereof that is specific for CD38, CD39, or CD157.

In at least one embodiment, the adenosine overexpressing disease state is a cancer, including, without limitation, a solid tumor cancer. Perhaps more specifically and without any intended limitation, the disease state may be lung cancer, prostate cancer, or glioblastoma. The antigen binding domain or fragment thereof may be specific for CD73 and/or the target cell may be a T regulatory cell, a cancer cell, or a malignant cell in a tumor microenvironment.

Methods of the present disclosure may further comprise the steps of: obtaining, or having obtained, a sample comprising blood cells, stem cells, or induced pluripotent stem cells (iPSCs); isolating, or having isolated, the blood cells, stem cells, or iPSCs from the sample; and transducing or transfecting the isolated cells with an expression vector containing the first polynucleotide construct to achieve the first population of engineered cells that express the first polynucleotide construct. In at least one embodiment, the sample is obtained from the subject or a donor separate from the subject. Accordingly, the step of administering, or having administered, to a subject a therapeutically effective amount of a pharmaceutical composition may comprise performing, or having performed, adoptive cell therapy.

BRIEF DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIG. 1B showing an explanatory schematic of the mechanism of tumor killing effected by such construct; and FIG. 1C showing a 3D structure of a translated protein of the aforementioned construct (modeled in RaptorX and images generated in Chimera), wherein the antigen binding region is a CD73-binding region;

Figure 1A:
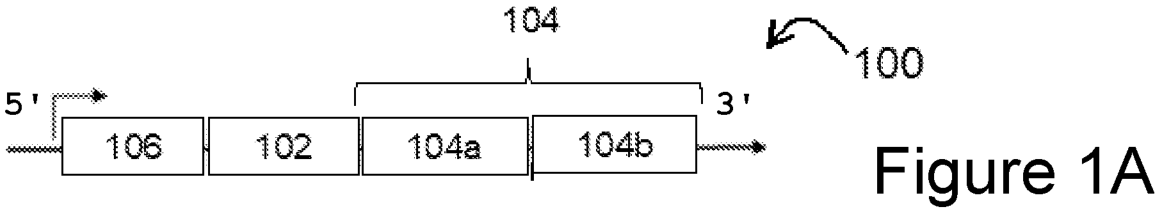
FIGS. 1A-1C illustrate a schematic and the mechanism of action of a construct according to at least one embodiment of the present disclosure, with FIG. 1A showing a schematic of the components of at least one embodiment of such construct.

While the present disclosure is susceptible to various modifications and alternative forms, exemplary embodiments thereof are shown by way of example in the drawings and are herein described in detail.

BRIEF DESCRIPTION OF THE SEQUENCE LISTINGS

SEQ ID NO: 1 is an amino acid sequence of a signal peptide:

```
METDTLLLWVLLLWVPGSTG;
```

SEQ ID NO: 2 is an artificial amino acid sequence of at least one embodiment of an antigen binding domain of the present disclosure that specifically binds CD73 and comprises a scFv:

```
EVQLLESGGGLVQPGGSLRLSCAASGFTFSSYAYSWVRQAPGKGLEWVSAI
SGSGGRTYYADSVKGRFTISRDNSKNTLYLQMNSLRAEDTAVYYCARLGYG
RVDEWGRGTLVTVSSGGGGSGGGGSGGGGSQSVLTQPPSASGTPGQRVTIS
CSGSLSNIGRNPVNWYQQLPGTAPKLLIYLDNLRLSGVPDRFSGSKSGTSA
SLAISGLQSEDEADYYCATWDDSHPGWTFGGGTKLTVL;
```

SEQ ID NO: 3 is an amino acid sequence of a FCyRIIIa stimulatory domain of an NK cell having a truncated FCRyIII extracellular domain+a transmembrane domain+a cytoplasmic domain:

```
ITQGLAVSTISSFFPPGYQVSFCLVMVLLFAVDTGLYFSVKTNIRSSTRDW
KDHKFKWRKDPQDK;
```

SEQ ID NO: 4 is an amino acid sequence of a protease-sensitive linker as follows:

```
LSGRSDNH;
```

SEQ ID NO: 5 is an amino acid sequence of a protease-sensitive linker (SEQ ID NO: 4) flanked by a (Gly-Ser)$_3$ linker and a short Gly-Ser spacer as follows:

```
GGGGSGGGGSGGGGSLSGRSDNHGSSGT;
```

SEQ ID NO: 6 is a nucleic acid sequence of a signal that encodes the peptide of SEQ ID NO: 1:

```
ATGGAACCCTGGCCCCTGCTGCTGCTGTTTAGCCTGTGCTCTGCTGGACTG
GTGCTGGGC;
```

SEQ ID NO: 7 is an artificial nucleic acid sequence that encodes a CD73-specific antigen binding domain fused with an scFv (CD73 scFv):

```
GAGGTGCAGCTGCTGGAATCTGGCGGGGGCCTGGTGCAGCCAGGAGGCTCC
CTGAGGCTGTCTTGCGCAGCAAGCGGCTTCACCTTTAGCTCCTACGCCTAT
TCCTGGGTGAGACAGGCACCTGGCAAGGGCCTGGAGTGGGTGTCTGCCATC
TCCGGCTCTGGCGGCAGGACATACTATGCCGACAGCGTGAAGGGCCGGTTC
ACCATCTCCAGAGATAACTCTAAGAATACACTGTACCTGCAGATGAACTCC
CTGAGGGCAGAGGACACCGCCGTGTACTATTGCGCAAGGCTGGGATATGGA
AGGGTGGATGAGTGGGGAAGGGGCACCCTGGTGACAGTGTCTAGCGGAGGA
```

-continued

```
GGAGGATCTGGAGGAGGAGGAAGCGGCGGAGGACGCAGCCAGTCCGTGCTG
ACACAGCCACCTTCTGCCAGCGGAACCCCTGGACAGAGGGTGACAATCTCC
TGTTCTGGCAGCCTGTCCAACATCGGCCGCAACCCAGTGAATTGGTACCAG
CAGCTGCCAGGAACCGCACCAAAGCTGCTGATCTATCTGGACAATCTGCGG
CTGAGCGGCGTGCCCGATAGATTTTCTGGCAGCAAGTCCGGCACATCTGCC
AGCCTGGCAATCAGCGGCCTGCAGTCCGAGGACGAGGCAGATTACTATTGT
GCCACCTGGGATGACTCTCACCCTGGCTGGACTTTCGGGGGAGGAACTAAA
CTGACCGTGCTG;
```

SEQ ID NO: 8 is a nucleic acid sequence that encodes a native Fcγ-stimulatory domain of an NK cell (FCyRIIIa) and a truncated extracellular domain:
ATTACCCAGGGCCTGGCGGTGAGCACCATT-
AGCAGCTTTTTTCCGCCGGGCTATCAG
GTGAGCTTTTGCCTGGT-
GATGGTGCTGCTGTTTGCGGTGGATACCGGCCTGT-
ATTTT AGCGTGAAAACCAACAT-
TCGCAGCAGCACCCGCGATTGGAAAGATCATAAATT-
TAA ATGGCGCAAAGATCCGCAGGATAAA; and SEQ ID NO: 9 is an artificial fusion nucleic acid sequence of at least one embodiment of the present disclosure comprising SEQ ID NO: 6 fused with SEQ ID NO: 7 and SEQ ID NO: 8 (signal. CD73.FcγRIIIa):

```
AAGCTTGCCACCATGTGGCAGCTGCTGCTGCCTACCGCTCTGCTGCTGCTG
GTCTCCGCCGAAGTCCAGCTGCTGGAAAGTGGGGGGGGCCTGGTCCAGCCA
GGAGGCAGCCTGAGGCTGTCCTGCGCAGCATCTGGCTTCACCTTTAGCTCC
TACGCCTATTCTTGGGTGAGACAGGCACCAGGCAAGGGCCTGGAGTGGGTG
AGCGCCATCAGCGGATCCGGAGGCAGGACATACTATGCCGACTCCGTGAAG
GGCCGGTTTACCATCAGCAGAGATAACTCCAAGAATACACTGTACCTGCAG
ATGAACTCCCTGAGGGCAGAGGACACCGCCGTGTACTATTGCGCAAGGCTG
GGATATGGAAGGGTGGATGAGTGGGGAAGGGGCACCCTGGTGACAGTGTCT
AGCGGAGGAGGAGGATCCGGAGGAGGAGGATCTGGCGGCGGCGGCTCTCAG
AGCGTGCTGACCCAGCCACCTTCCGCCTCTGGAACCCCAGGCCAGAGGGTG
ACAATCAGCTGTTCCGGCTCTCTGAGCAACATCGGCCGCAACCCTGTGAAT
TGGTACCAGCAGCTGCCTGGCACCGCCCCAAAGCTGCTGATCTATCTGGAC
AATCTGCGGCTGTCTGGCGTGCCTGATAGATTTTCCGGCTCTAAGAGCGGC
ACATCCGCCTCTCTGGCCATCTCTGGCCTGCAGAGCGAGGACGAGGCCGAT
TACTATTGCGCAACCTGGGACGATAGCCACCCAGGATGGACATTCGGCGGA
GGAACCAAGCTGACAGTGCTGATCACCCAGGGCCTGGCCGTGAGCACAATC
TCCTCTTTCTTTCCACCCGGCTACCAGGTGTCCTTCTGTCTGGTCATGGTG
CTGCTGTTTGCCGTGGACACCGGCCTGTATTTCAGCGTGAAGACAAATATC
AGATCATCAACAAGAGATTGGAAAGACCATAAGTTCAAGTGGCGGAAGGAC
CCCCAGGACAAGTGACTCGAG.
```

In addition to the foregoing, the above-described sequences are provided in computer readable form encoded in a file filed herewith and herein incorporated by reference. The information recorded in computer readable form is identical to the written Sequence Listings provided above, pursuant to 37 C.F.R. § 1.821(f).

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

A "subject" or "patient" as the terms are used herein is a mammal, preferably a human, and is inclusive of male, female, adults, and children.

"Nucleic acid" refers to deoxyribonucleotides or ribonucleotides and polymers thereof in either single- or double-stranded form and complements thereof. The term encompasses nucleic acids containing known nucleotide analogs or modified backbone residues or linkages, that are synthetic, naturally occurring, and non-naturally occurring, have similar binding properties as the reference nucleic acid, and metabolized in a manner similar to the reference nucleotides.

The terms "polypeptide," "peptide," and "protein" are used interchangeably herein (unless expressly stated otherwise) to refer to a polymer of amino acid residues, a polypeptide, or a fragment of a polypeptide, peptide, or fusion polypeptide. The terms apply to amino acid polymers in which one or more amino acid residue is an artificial chemical mimetic of a corresponding naturally occurring amino acid, as well as to naturally occurring amino acid polymers and non-naturally occurring amino acid polymers.

As used herein, "adenosinergic" means working on adenosine.

"Chimeric antigen receptor" or "CAR" molecules are recombinant fusion proteins and distinguished by their ability to both bind antigen (e.g., CD39/CD79) and transduce activation signals via co-stimulatory domains such as those utilizing immunoreceptor activation motifs (ITAMs) present in the cytoplasmic tails. Gene constructs utilizing an antigen-binding moiety (e.g., generated from single chain antibodies (scFv)) afford the additional advantage of being "universal" in that they bind native antigen on the target cell surface in an human leukocyte antigen (HLA)-independent fashion, therefore they do not need to be collected from a patient or a specific HLA-matched donor.

A chimeric antigen receptor according to the embodiments of the present disclosure can be produced by any means known in the art, though preferably it is produced using recombinant DNA techniques. A nucleic acid sequence encoding the several regions of the chimeric antigen receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic or autologous NK cells.

An "antibody fragment" as used herein means a portion of an intact antibody, preferably the antigen-binding or variable region of the intact antibody. Examples of antibody fragments include, for example, single-chain antibody molecules (scFv), or nanobodies. While in the present disclosure reference is made to antibodies and various properties of antibodies, the disclosure applies to functional antibody fragments as well unless expressly noted to the contrary.

Papain digestion of antibodies can produce a residual "Fc" fragment, a designation reflecting the ability to crystalize readily. The Fc fragment comprises the carboxy-terminal portions of both H chains held together by disulfides. The effector functions of antibodies are determined by sequences of the Fc region; this region is also the part recognized by Fc receptors found on certain types of cells.

"Fc receptor" or "FcR" as used herein describes a protein found on the surface of NK cells that contributes to the protective functions of the immune system. The preferred FcR is a native sequence human FcR. Moreover, a preferred FcR is one that binds an IgG antibody (a gamma receptor) and includes, without limitation, the receptor of FcγRIIIA or CD16 (an "activating receptor"), including allelic variants and alternatively spliced forms of this receptor. Activating receptor FcγRIIIA contains an ITAM in its cytoplasmic domain. Activation of FcγRIIIA causes the release of cytokines such as IFN-γ that signal to other immune cells and cytotoxic mediators like perforin and granzyme that enter the target cell and promote cell death by triggering apoptosis.

An antigen binding domain or fragment thereof the present disclosure "that binds" a target of interest is one that binds the antigen/target with sufficient affinity such that the protein, binding domain, or engineered cell is useful as a diagnostic and/or therapeutic agent in targeting a protein or a cell or tissue expressing the antigen. With regard to the binding of a protein, binding domain, and/or engineered cell to a target molecule, the term "specific binding" or "specifically binds to" or is "specific for" a particular polypeptide or an epitope on a particular polypeptide target means binding that is measurably different from a non-specific interaction. Specific binding can be measured, for example, by determining by competition with a control molecule that is similar to the target. In at least one embodiment, "specifically binds" refers to binding of the antigen binding domain to its specified adenosine-producing enzyme target receptors (e.g., CD73 or CD39) and not other specified non-target receptors.

"Purinergic receptors" as used herein refers to a family of plasma membrane molecules that are found in almost all mammalian tissues. Within the field of purinergic signaling, these receptors are involved in various cellular functions, including apoptosis and cytokine secretion. P1 receptors are a class of purinergic G protein-coupled receptors with adenosine as the endogenous ligand. There are four known types of adenosine receptors in humans: $A_1$, $A_{2A}$, $A_{2B}$, and $A_3$. $A_1$, $A_{2A}$, and $A_{2B}$ protein sequences are highly conserved across mammalian species (over about 80% identity), while $A_3$ is more variable. In humans, $A_1$, $A_{2A}$, and $A_3$ are considered as high affinity receptors for adenosine, while $A_{2B}$ receptor has a lower affinity for adenosine.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it is positioned so as to facilitate translation. Generally, "operably linked" means that the DNA sequences being linked are contiguous and, in the case of leader, contiguous and in a reading phase. However, enhancers do not necessarily have to be contiguous. Linking may be accomplished by ligation at convenient restriction sites. If such sites do not exist, synthetic oligonucleotide adaptors or linkers may be used in accordance with conventional practice.

"Percent (%) amino acid sequence identity" with respect to a reference to a polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity and not considering any conservative substitutions as part of the sequence identity. Alignment for purposes of determining percent amino acid sequence identity can be achieve din various ways that are within the skill of the art, for instance, using publicly available computer software. Those skilled in the art can determine appropriate parameters for aligning sequences, including any algorithms needed to achieve maximal alignment over the full length of the sequences being compared.

"Downregulation" or "down-regulated" may be used interchangeably and refer to a decrease in the level of a marker, such as a gene, nucleic acid, metabolite, transcript, enzyme, protein, or polypeptide, as compared to an established level (e.g., that of a healthy cohort or the subject of interest). "Upregulation" or "up-regulated" or "overexpressed" may also be used interchangeably and refer to an increase in the level of a marker, such as a gene, nucleic acid, metabolite, transcript, protein, enzyme, or polypeptide, as compared to an established level (e.g., that of a healthy control or the subject of interest). For example, relevant in the present application, CD39 and/or CD73 may be overexpressed in a patient experiencing a solid tumor or other cancer as compared to a healthy control.

A "marker" or "biomarker" as the terms are used herein may be described as being differentially expressed when the level of expression in a subject who is experiencing an active disease state is significantly different from that of a subject or sample taken from a healthy subject. A differentially expressed marker may be overexpressed or underexpressed as compared to the expression level of a normal or control sample or subjects' baseline (i.e. downregulated). The increase or decrease, or quantification of the markers in a biological sample may be determined by any of the several methods known in the art for measuring the presence and/or relative abundance of a gene product or transcript. The level of markers may be determined as an absolute value, or relative to a baseline value, and the level of the subject's markers compared to a cutoff index. Alternatively, the relative abundance of the marker or markers may be determined relative to a control, which may be a clinically normal subject.

The terms "treatment" or "therapy" as used herein (and grammatical variations thereof such as "treat, "treating," and "therapeutic") include curative and/or prophylactic interventions in an attempt to alter the natural course of the individual being treated. More particularly, curative treatment refers to any of the alleviation, amelioration and/or elimination, reduction and/or stabilization (e.g., failure to progress to more advanced stages) of a symptom, as well as delay in progression of a symptom of a particular disorder. Prophylactic treatment refers to any of the following: halting the onset, reducing the risk of development, reducing the incidence, delaying the onset, reducing the development, and increasing the time to onset of symptoms of a particular disorder. Desirable effects of treatment include, but are not limited to, preventing occurrence or recurrence of a disease, alleviation of symptoms, diminishment of any direct or indirect pathological consequences of the disease, preventing metastasis, decreasing the rate of disease progression, amelioration or palliation of the disease state, and remission or improved prognosis. In some embodiments, compositions of the present disclosure are used to delay development of a disease and/or tumor, or to slow (or even halt) the progression of a disease and/or tumor growth.

As used herein, the term "anti-tumor effective amount" refers to an effective amount of construct-expressing NK cells to reduce cancer cell or tumor growth or to decrease tumor volume or number of tumor cells in a subject. "An anti-tumor effective amount" can also refer to an effective amount of engineered NK cells or an engineered NK cell line to increase life expectancy or to alleviate physiological effects associated with the tumor or cancer.

As used herein, the phrases "therapeutically effective dose," "therapeutically effective amount," and "effective amount" means (unless specifically stated otherwise) a quantity of a polypeptide and/or engineered cells of the present disclosure which, when administered either one time or over the course of a treatment cycle, affects the health, wellbeing or mortality of a subject (e.g., and without limitation, a diminishment or prevention of effects associated with a cancerous condition). The a appropriate dosage or amount of a polypeptide, engineered cells, or other compound to be administered to a subject for treating a disease, condition, or disorder (including, without limitation, a cancerous condition such as a solid state tumor) as described herein will vary according to several factors including the type and severity of condition being treated, how advanced the disease pathology is, the formulation of the composition, patient response, the judgment of the prescribing physician or healthcare provider, whether one or more constructs are being administered, the route of administration, and the characteristics of the patient or subject being treated (such as general health, age, sex, body weight, and tolerance to drugs). Thus, the absolute amount of engineered cells included in a given unit dosage form can vary widely, and depends upon factors such as the age, weight and physical condition of the subject, as well as the method of administration.

A therapeutically effective amount is also one in which any toxic or detrimental effects of the therapeutic agent are outweighed by the therapeutically beneficial effects. In at least one embodiment, an anti-tumor effective amount may be a therapeutically effective dose.

Administered dosages for the engineered cells as described herein for treating cancer, a cancerous tumor, or other disease or disorder are in accordance with dosages and scheduling regimens practiced by those of skill in the art. Typically, doses $>10^9$ cells/patient are administered to patients receiving adoptive cell transfer therapy. Determining an effective amount or dose is well within the capability of those skilled in the art, especially in light of the detailed disclosure provided herein.

The term "pharmaceutical composition" means a composition comprising one or more of engineered cells or engineered NK cell lines as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents, and dispensing agents (depending on the nature of the mode of administration and dosage forms).

The term "pharmaceutically acceptable" and grammatical variations thereof, as they refer to compositions, carriers, diluents, reagents, and the like, are used interchangeably and represent that the materials are capable of administration to or upon a mammal without undue toxicity, irritation, allergic response, and/or the production of undesirable physiological effects such as nausea, dizziness, gastric upset, and the like as is commensurate with a reasonable benefit/risk ratio. In other words, it is a material that is not biologically or otherwise undesirable—i.e. the material may be administered to an individual along with NK cells (and/or stem cells or iPSCs) modified to express the constructs of the present disclosure without causing any undesirable biological effects or interacting in a significantly deleterious manner with any of the other components of the pharmaceutical composition in which it is contained.

The term "isolated" means that the material is removed from its original environment, e.g., the natural environment if it is naturally occurring. For example, a naturally occurring NK cell present within a living organism is not isolated, but the same NK cell separated from some or all of the coexisting materials in the natural system is isolated.

The inventive concepts of the present disclosure generally relate to methods, compositions, and engineered peptides for the treatment of cancers, particularly solid tumor cancers, by concurrent modulation of a cancerous immunometabolic pathway through 1) a targeted adenosine producing cell surface protein blockade to restore anti-tumor responses, and 2) immunotherapy of adenosine-producing solid tumors via CD73 or similar adenosine-producing cancer associated enzymes with engineered natural killer (NK) cells in vivo. This novel approach combines the inhibition of adenosine producing enzymes with the triggering of cytotoxicity in a single agent, thereby promoting intratumoral infiltration and targeting of solid tumors by the novel engineered NK cells described herein.

In at least one exemplary embodiment, a novel construct is provided (e.g., CD73.FcγRIIIa) that redirects purinergic signaling through local single-agent engagement of CD73 in situ while promoting NK-mediated lysis through Fcγ-receptor signaling or equivalent signaling mechanisms of an NK cell. The compositions and methods of the present disclosure may be employed alone or used to boost the efficacy of other anti-cancer therapies. Further, in at least one exemplary embodiment, intracellular signaling (provided by CD3ζ, for example) is added to the novel compositions of the present disclosure to enhance killing stimulus.

Brief descriptions of the relevant cellular pathways and mechanisms will be provided to aid in understanding of the inventive concepts hereof, followed by a detailed description of the present constructs, compositions, and novel methods provided herein.

Adenosine

Contributing to the pathogenesis of solid tumors are elevated concentrations of adenosine, a consequence of anaerobic glycolysis in hypoxic solid tumor cores. In solid tumors, ATP is abundantly released in the extracellular space where its concentration can reach a few hundred micromole per liter, a concentration more than a thousand times higher than in healthy tissues. This phenomenon is mainly due to cell death in the tumor core and to metabolic or hypoxic stress and pro-inflammatory signals that stimulate active export of ATP. In the tumor microenvironment ("TME"), extracellular ATP acts as a danger signal involved in the recruitment of innate immune cells and in the priming of anti-tumor activity. However, in the TME, the extracellular ATP is degraded into immunosuppressive adenosine via the concerted enzymatic activity of at least CD39 and CD73, as well as CD38. As a consequence, in various solid tumors, accumulation of extracellular adenosine followed by engagement of the adenosine receptors on tumor-reactive NK cells is a highly immunosuppressive mechanism that drives tumor growth.

CD39 and CD73 are ecto-nucleoside triphosphoate diphosphohydrolases, which are anchored cell surface proteins, and exhibit a catalytic site facing the extracellular space. CD38 and CD157 are alternative pathways that are also surface molecules with an extracellular catalytic domain, except theirs consists of ADP ribosyl-cyclases. Expression of these ectoenzymes by solid tumors and in the TME results in the production of extracellular adenosine.

CD39 is anchored to the cell membrane via two transmembrane domains that are essential for maintaining the catalytic activity and specificity for the substrate. CD73 is a GPI-anchored enzyme. Whereas CD39 catalyzes the hydrolysis of extracellular ATP (or ADP) to adenosine monophosphate (AMP), CD73 is the rate-limiting enzyme in adenosine generation pathways and dephosphorylates AMP to adenosine, ultimately liberating it into the extracellular space.

CD38 and CD157 are part of the same family of NADase/ADPR cyclase enzymes. CD38 is a surface glycoprotein characterized by a relatively large extracellular domain that harbors the catalytic site. CD157, on the contrary, is attached to the membrane via a glycosylphosphatidylinositol anchor. The extracellular domain of both molecules contains conserved critical residues. They both metabolize nicotinamide dinucleotide ($NAD^+$), which also affects purinergic receptors and converge on adenosine generation with profound effects generating immune effectors cells (e.g., NK cells) towards tolerance. Indeed, extracellular $NAD^+$ can be degraded by an integrated network of ectonucleotidases, including CD38 and CD157, which generate intermediates that modulate signaling and activate immunoregulatory circuits. Extracellular adenosine can be generated from NAD+ through to the coordinated action of CD38, which generates ADP ribose (ADPR) and PC-1 (ectonucleotide pyrophosphatase/phosphodiesterase family member 1), which generates AMP. Similar CD38, CD157 generates cADPR and subsequent ADPR when incubated with $NAD^+$.

In human peripheral blood, both CD39 and CD73 are typically expressed on about 2-5% of NK cells within non-malignant blood cells. As such, expression of both CD39 and CD73 is virtually absent from circulating human NK cells in healthy individuals. However, significant expression of CD39 by human tumors and infiltrating immune cells has been widely described, which is associated with generation of adenosine that has an inhibitory role on effector anti-tumor immunity and exposure to proinflammatory cytokines, oxidative stress and hypoxia. Likewise, expression of CD73 remains at constitutively high levels on many types of cancer cells. High CD73 expression has been shown to be correlated with unfavorable clinical outcomes, which is consistent with the immunosuppressive role of adenosine. The expression of CD38, CD73, and/or CD157 may also be upregulated, especially in a TME that is hypoxic.

Accordingly, CD39 and CD73 are overexpressed on many solid tumor cells and implicated in the promotion of cancer progression through upregulation of adenosine signaling following dephosphorylation of extracellular AMP. As described in further detail below, adenosinergic signaling interferes with the trafficking and activities of NK cells due to the heterologous desensitization of chemokine receptors and reduced proinflammatory cytokines and inhibits the exocytosis of cytotoxic NK granules. This creates a pro-angiogenic niche supporting tumor development.

Adenosine-induced immunosuppression can be alleviated by antibody-mediated blockade of CD73; however, this alone relies on the recruitment of NK cells to hypoxic tumor niches. Conventional efforts have not targeted adenosinergic signaling in conjunction with NK-based immunotherapy.

NK Activity

NK cells, specialized effectors of the innate immune system, can respond rapidly to cancer cells due to expression of germline-encoded activating receptors capable of directly binding to pathogen-derived or stress-induced self-antigens. The activity of NK cells is controlled by a balance of signals from a repertoire of activating and inhibitory receptors. Activating receptors include, without limitation, natural cytotoxic receptors (NCRs), natural killer group 2 member D (NKG2D), CD16 (FcγRIIIA), FasL, TRAIL, and co-stimulatory receptors such as LFA-1, CD244 (2B4), and CD137 (41BB). These activating cell surface receptors have the capacity to trigger cytolytic programs, as well as cytokine and chemokine secretion via intra-cytoplasmic ITAMs such as 2B4, 41BB, and/or via other transmembrane signaling adaptors.

Conversely, inhibitory NK cell receptors predominantly recognize cognate MHC class I protein and provide self-tolerance toward healthy cells. Cells with absent or reduced expression of MHC class I protein, as often observed after transformation or viral infection, are unable to trigger sufficient inhibitory signals and become susceptible to NK cell attack.

Upregulated expression of ligands for activating NK cell receptors can render cells sensitive to NK cell attack. Once such activating receptor is the C-type lectin-like receptor NKG2D. NKG2D receptor is expressed in NK cells as well as many T cells, such as NKT cells, CD8+ T cells, and γδT cells. However, in T cells, the NKG2D usually acts only as a costimulatory receptor and does not directly mediate cytotoxicity, which is different from NK cells. Expression of NKG2D ligands (often expressed in tumor cells) is generally regarded as a “danger signal,” marking cells for immune attack, and activating NK cells by binding to the NKG2D receptor. Indeed, ex vivo studies with human cells and in vivo tumor models in mice demonstrated that expression of NKG2D ligands on tumor cells results in an increased susceptibility to NK cell attack. Where the immune system is properly functioning, ligation of NKG2D on NK cells serves to promote NK cell activation and influence the adaptive immune response; however, there are various mechanisms that inhibit the action of NKG2D receptor/NKG2D ligand to enable immune escape of tumor cells.

Direct cytotoxicity for target cells by NK cells is thought to rely on cytolytic granules such as perforin and granzymes. The death receptor (DR) mediated apoptotic process of abnormal or stressed cells is also a way of direct killing. The caspase enzymatic cascade induced apoptosis is triggered by the interaction between DRs expressed on NK cells (e.g., FasL, TRAIL) and their ligands on target cells.

Another direct killing mechanism involves antibody dependent cell-mediated cytotoxicity (ADCC), which is usually mediated by immunoglobulin G (IgG) in humans. The Fab moiety and Fc moiety of the antibody bind to the tumor-associated antigens on the tumor cell and CD16A (FcγRIIIA), the activating receptor expressed on NK cells, respectively, to form an immunological synapse between the two. The NK cells are thereafter activated and secrete cytotoxic granules to kill the tumor cells. Notably, in humans, FcγRIIIA is the primary receptor for NK mediated ADCC. In addition to the foregoing, NK cells can also function through an indirect way by producing chemokines and cytokines to kill abnormal cells and regulate innate and acquired immune responses.

As the present inventors previously described in Wang et al., *Purinergic Targeting Enhances Immunotherapy of CD73+ Solid Tumors with PiggyBac-engineered Chimeric Antigen Receptor Natural Killer Cells*, J for ImmunoTherapy of Cancer 6: 136 (2018), which is incorporated herein by reference, administration of a CD73 antibody enhanced the effector function of chimeric antigen receptor (CAR)-engineered NK cells both in vitro and in vivo. However, contributing to immunodeficiency in and hindering adoptive immunotherapy with NK cells, is the downregulation of activating receptors caused by the solid tumor milieu which significantly stunts NK cell infiltration and limits their cytolysis.

As discussed above, adenosine signaling results in downregulation of receptor expression on NK cells (for example, and without limitation, it has been established that adenosine downregulates NKG2D on cytokine-primed human NK cells). In addition to extracellular adenosine concentrations, the expression of NKG2D receptor on NK cells can be regulated by a variety of other factors, including changes in cellular activity factors and the physicochemical features of the TME (such as, for example, hypoxia). The TME is composed of a variety of cells and molecules, including tumor-associated fibroblasts, tumor-associated macrophages, Tregs, immunoregulatory enzymes (e.g., arginase and cyclooxygenase-2), and immunosuppressors (e.g., interleukin-10 (IL-10), transforming growth factor-β (TGF-β), vascular endothelial growth factor (VEGF), prostaglandin $E_2$ ($PGE_2$), and programmed death ligand 1). Tumor cells and immunosuppressive cells express or secrete podocalyxin-like protein 1 ($PCLP_1$) activin-a, indoleamine-pyrrole 2, 3-dioxygenase (IDO), $PGE_2$, TGF-β, and macrophage migration inhibitory factor (MIF) in the TME to mediate NKG2d downregulation.

Furthermore, hypoxia is an important feature of the TME that can directly or indirectly induce the secretion of immunosuppressive molecules, such that NK cells lose the ability to upregulate NKG2D expression through IL-2 and other cytokines. Under hypoxic conditions, tumor cells can secrete a variety of chemokines to recruit immunosuppressive cells that secrete cytokines, such as TGF-β for example, thereby downregulating NKG2D expression. Additionally, in tumor cells, hypoxia stress induces upregulation of the transcription factor NANOG, which can directly bind to the TGF-β promoter region and upregulate TGF-β expression.

Constructs and Related Methods

The inventive constructs, engineered NK cells and NK cell lines, compositions and methods of the present disclosure uniquely redirect adenosinergic immunometabolic inhibition through direct NK cell engagement and, thus, significantly enhance the duration of tumor suppression. This approach combines the specificity of engineered NK cells with the immune engagement induced by a blockade of adenosine producing enzymes (e.g., anti-CD38, anti-CD39, anti-CD73, and anti-CD157). Accordingly, the constructs, engineered NK cells, pharmaceutical compositions and resulting therapies of the present disclosure yield combination immunotherapy modalities that redirect purinergic signaling in situ and concurrently suppress tumor progression through activation of NK cytotoxicity and/or cytolysis.

Now referring to FIG. 1, at least one exemplary embodiment of a synthetic genetic construct 100 is provided. The genetic construct 100 is engineered so that the NK cells and NK cell lines that express it (achieved via bioengineering and other known modalities) express at least one domain and/or receptor that are not normally expressed on the surface of native NK cells. The binding of these modified NK cells and NK cell lines to ligands on target cells, such as tumor cells, is through new domains not present in native NK cells. In at least one embodiment, the construct 100 may comprise a CAR construct.

In perhaps its simplest form, the genetic construct 100 comprises a first sequence that encodes an antigen binding domain or fragment thereof 102 ($V_L/V_H$) fused with (or operably linked to) a second sequence that encodes one or more stimulatory or costimulatory domains 104 of an NK cell. The antigen binding receptor 102 is specific for an adenosine-producing or an adenosine-intermediary-producing cell surface protein of a target cell and it is the antigen binding receptor 102 that binds such target cell in application. The stimulatory or costimulatory domain(s) 104 of a NK cell are ones that promote cytotoxic and/or cytolytic activity of the engineered cell or cell line upon activation.

The antigen binding domain or fragment thereof 102 is specific for an adenosine producing cell surface protein of a target cell or an adenosine-intermediary producing cell surface protein of a target cell. For example, such adenosine or adenosine-intermediary producing cell surface protein may comprise CD38, CD39, CD73, CD157 or any other cell surface protein of a target cell that produces adenosine or an intermediary thereof. The antigen binding domain 102 can comprise complimentary determining regions, variable regions, and/or antigen binding fragments thereof, as desired.

The target cell may comprise any cell that produces adenosine or an intermediary thereof through a cell surface protein, for example, and without limitation, a T regulatory cell, a cancer cell, or otherwise malignant cells within a TME. As described in detail above, such cells produce adenosine through CD73 and, as such, the antigen binding domain 102 may be specific for CD73 (CD73-targeted). Additionally or alternatively, the construct 100 may act to disrupt the adenosine generation pathway further upstream through inhibition of CD38, CD39 (which catalyzes the hydrolysis of extracellular ATP (or ADP) to AMP), and/or CD157. Accordingly, in at least one exemplary embodiment, the antigen binding domain 102 may be specific for binding CD39 (CD39-targeted), CD38 (CD38-targeted), specific for CD157 (CD157-targeted), and/or variants of any of the foregoing. As these targets (and, in particular, CD73) are upregulated in cancer cells and the TME, the inclusion of an antigen binding domain or fragment thereof 102 in the construct 100 that has specificity to any of the aforementioned cell surface proteins allows for the resulting engineered NK cells to directly target and recognize cancer and other such cells. To this end, the present constructs 100 enhance specificity and allow for the direct targeting and engagement of tumor, cancer and other malignant cells safely.

The antigen binding domain 102 may further comprise one or more single-chain variable fragment (scFv) sequences or other antibody fragments such as nanobodies, which are fusion proteins between the variable regions of the heavy ($V_H$) and light ($V_L$) chains of immunoglobulins, connected with a shorter linker peptide of about ten to about 25 amino acids. The specific configuration of the scFv or other antibody fragments may be selected based on desired properties of the resulting peptide (e.g., rich in glycine for flexibility, as well as serine or threonine for solubility). As is known in the art, the scFv or another antibody fragment can either connect the N-terminus of the $V_H$ with the C-terminus of the $V_L$, or vice versa. The protein retains the specificity of the original immunoglobulin, despite removal of the constant regions and introduction of the scFv or other antibody fragments.

Accordingly, in at least one embodiment, the antigen binding region or domain 102 comprises a fragment of a scFv derived from a particular mouse, or human, or humanized monoclonal antibody or pursuant to other known sources and known methodologies. The fragment can also be any number of different antigen-binding domains of an antigen-specific antibody. In a more specific embodiment, the fragment is an antigen-specific scFv (e.g., CD39 scFv, CD73 scFv, CD38 scFv, or CD157 scFv) encoded by a sequence that is optimized for human codon usage for expression in human NK cells. In at least one exemplary embodiment, the first sequence of the construct is SEQ ID NO: 7, and the antigen binding domain or fragment thereof 102 that it encodes CD73 scFv having SEQ ID NO: 2. FIG. 1C shows the structure of a translated protein comprising a CD73 scFv-binding region 102.

Referring back to the sequent second sequence of the construct 100 that encodes the one or more stimulatory or costimulatory domains 104, the first sequence (encoding the antigen binding domain 102) is operably linked thereto (directly or via a hinge region as described below). The one or more stimulatory or costimulatory domains 104 comprise an NK activator receptor or receptor complex capable of triggering the cytolytic and cytotoxic programs of the NK cell upon the antigen binding domain or fragment thereof 102 binding a target cell. For example, the stimulatory or costimulatory domains 104 may comprise a Fc signal molecule. Additionally or alternatively, in certain embodiments, the stimulatory or costimulatory domains 104 may comprise FcγRIIIA, FasL, TRAIL, NKG2D, CD28, 4-1BB, OX40, LFA-1, CD244, CD137, or the NKG2D-DAP10 receptor complex, and CD3ζ. Furthermore, the stimulatory or costimulatory domains 104 may also comprise additional other costimulatory domains including, without limitation, one or more of DAP12, NKp46, NKp44, NKp30, and DAP10.

In at least one exemplary embodiment, the stimulatory or costimulatory domains 104 comprises FcγRIIIA (SEQ ID NO: 8) and the cytotoxic signal is transmitted upon antigen binding domain 102 engagement via NK cell-associated scFv via intracellular signaling through the FcγRIIIA cascade.

In application, engagement of the antigen binding domain 102 of the construct 100 with the target cell promotes signaling through the stimulatory or costimulatory domains 104 of the engineered NK cell, resulting in activation of ITAM motifs on CD3 adaptor chains (see, e.g., FIGS. 1A and 1B) to trigger NK cell-mediated cytotoxicity against solid tumor and other adenosine producing or adenosine-intermediary producing targets. Accordingly, when the engineered NK cell directly targets and binds an adenosine or adenosine-intermediary producing surface cell protein (on a solid tumor, for example), signals are sent to the engineered NK cell via the stimulatory or costimulatory domains 104 (e.g., via FcγRIIIA) to trigger cytolysis and/or cytotoxicity mechanisms of the target (cancer) cell that it has bound.

In at least one embodiment, the stimulatory or costimulatory domains 104 may comprise at least two domains. For example, the antigen binding domain 102 is operably linked with a transmembrane domain 104*a* and an intracellular domain 104*b* of the engineered cell. Additionally, the stimulatory or costimulatory domains 104 may further comprise an extracellular domain 104*c* (not shown) which is linked to the intracellular domain 104*b* by the transmembrane domain 104*a*. In at least one embodiment, the stimulatory or costimulatory domains 104 comprise a Fc-receptor. FIG. 1C shows a structure of a translated protein of such an embodiment, there having transmembrane and intracellular domains 104*a*, 104*b* of FcγRIIIA.

Now referring to the intracellular domain 104*b*, in certain embodiments, the intracellular domain 104*b* is responsible for activation of at least the cytotoxic or cytolytic activity of the NK cell engineered to express the construct 100. Accordingly, as used herein, the term "intracellular domain 104*b*" refers to the portion of a protein/receptor molecule that transduces the effector function signal and directs the NK cell to perform a specialized function—here, deploying the killing mechanism. While usually the entire intracellular signaling domain 104*b* will be employed, in many cases it may not be necessary to use the entire intracellular polypeptide. To the extent that a truncated portion of the intracellular domain may be used, such truncated portion may be used in place of the intact chain as long as it still transduces the cytotoxicity and/or cytolytic signal(s) as desired. The term "intracellular domain" is thus meant to include a truncated portion of the intracellular domain sufficient to transduce the effector function signal, upon the engineered NK cell binding to a target. Where the stimulatory or costimulatory domains 104 comprises FcγRIIIA, it is noteworthy that association of the intracellular domain of FcγRIIIA with native CD3ζ triggers enhanced NK-mediated cytotoxicity.

The extracellular domain 104*c* may be complete or truncated. Where the one or more stimulatory or costimulatory domains 104 comprises an extracellular domain 104*c*, where the extracellular domain 104*c* extends from the membrane of the NK cell and is positioned between the antigen binding domain 102 and the transmembrane domain 104*a*. Depending on the specific stimulatory or costimulatory domain(s) 104 employed, it may be desirable to truncate the extracellular domain 104*c* to achieve a desired configuration and/or efficacy; however, it may not be necessary to truncate the extracellular domain 104*c*, depending the type of stimulatory or costimulatory domains 104 used (in other words, depending on the configuration/length of the extracellular domain 104*c*). In at least one exemplary embodiment, the stimulatory or costimulatory domains 104 of the construct 100 comprise a truncated extracellular domain 104*c* of FcγRIIIA comprising about 189-208 amino acids. In at least one embodiment, for example, the stimulatory or costimulatory domains 104 comprise SEQ ID NO: 3. In certain specific aspects, the stimulatory or costimulatory domains 104 can be 85%, 90%, 91%, 92%, 93%, 94%, 95%, 96%, 97%, 98%, 99% or 100% identical to SEQ ID NO: 3.

Optionally, the construct 100 can additionally include a hinge domain (not shown) positioned between the antigen binding domain 102 and the stimulatory or costimulatory domains 104. A hinge domain may comprise one or more sequences that encode linkers or spacers and may be included in the construct, for example, to provide sufficient distance between the antigen binding domain 102 and the membrane and/or cell surface. Additionally or alternatively, a hinge domain may be included (and/or configured) to facilitate a desired tertiary structure and/or alleviate possible steric hindrance that could adversely affect antigen binding or effector function of the modified NK cells. In this manner, the hinge domain can be used and/or manipulated for optimal expression in human cells.

Additional embodiments of the construct 100 may further comprise one or more sequences for encoding one or more cytokine molecules positioned downstream of the stimulatory or costimulatory domains 104 to improve persistence of the resulting engineered NK cells. Such cytokine molecules may comprise, for example, IFN-γ, IL-2, IL-12, IL-15, IL-18, and/or IL-21. Because even native NK cells require certain cytokines to survive, including a sequence for one or more cytokine molecules in the construct 100 may be beneficial. Alternatively, any necessary cytokine molecules may simply be infused into the patient using soluble cytokines.

Additionally or alternatively, additional intracellular signaling domains may be added to the construct 100 to enhance killing stimulus (i.e. further bolster the NK-mediated cytotoxicity of the resulting engineered NK cells). For example, the human CD3ζ intracellular domain can be operably linked with the antigen binding domain 102 and the stimulatory or costimulatory domains 104. Other cytoplasmic domains may also be employed as desired, with one or multiple of such cytoplasmic domains fused together for additive or synergistic effect, if desired.

An exemplary embodiment of the construct 100 has SEQ ID NO: 9 and comprises the following components in frame from 5' end to 3' end: an anti-CD73 scFv sequence (for example, in at least one embodiment, SEQ ID NO: 7), a truncated extracellular domain of FCyRIIIa (AA 189-208) the transmembrane domain of FCyRIIIa and an intracellular domain of FCyRIIIa (costimulatory domain 104 collectively, in at least one embodiment, SEQ ID NO: 8). Furthermore, certain embodiments of such construct 100 may comprise a sequence 85%, 90%, 91%, 92%, 93%, 94%, 95%, 96%, 97%, 98%, 99% or 100% identical to SEQ ID NO: 9.

In the setting of an antibody blockade, native NK cells signal through the expression of immunoglobulin Fc receptors, particularly the activating receptor FcγRIIIA (CD16a), to mediate ADCC. FcγRIIIA engagement triggers the phosphorylation of intracytoplasmic ITAMs on adaptor chains CD3ζ and FcRγ through γ- and ζ-chains of FcγRIIIA. The ensuing signaling process results in cytolytic signals, cytotoxic granule release (such as perforin and granzymes) and cytokine production, which results in direct cytotoxicity for target cells.

In operation, the antigen binding receptor 102 directly targets the cell(s) of interest and, when the antigen binding receptor 102 binds the targeted cell, the engineered NK cell signals via the stimulatory or costimulatory domains 104 signals to trigger cytolysis and/or cytotoxicity of the target cell in the absence of endogenous ADCC. In other words, the construct 100 allows for bypassing other natural cytotoxicity receptors. Incorporating the stimulatory or costimulatory domains 104 enables the engineered NK cells, after they have associated with the adenosine producing or adenosine-intermediary producing cell surface proteins of the target cell, to activate the cytotoxicity/cytolysis signaling pathways through an alternative approach. Accordingly, the present genetic construct 100 and resulting engineered NK cells and NK cell lines combine NK cell mediated activation with target-specific recognition.

These inventive techniques are uniquely advantageous over conventional approaches. Primarily, allogenic stem cells and NK cells cause no graft versus host disease, making their widespread, off-the-shelf use feasible. Mature NK cells have a relatively limited lifespan, permitting effective antitumor activity while reducing the probability of long-term adverse events such as on-target/off-tumor effects. Further, expression of the present constructs can increase the specificity and the cytotoxicity of NK cells against cancer targets and rescue the downregulation of activating receptors induced by suppressive TME mechanisms such as hypoxia. NK cells also have a better safety profile as they can avoid in vivo cytokine storm and lack clonal expansion.

The constructs according to the embodiments can be prepared using conventional techniques. Because, for the most part, natural sequences may be employed, the natural genes may be isolated and manipulated, as appropriate, to allow for the proper joining of the various components. For example, the nucleic acid sequences can be isolated by employing the polymerase chain reaction (PCR), using appropriate primers that result in deletion of the undesired portions of the gene. Alternatively, restriction digests of cloned genes can be used to generate the chimeric construct. In either case, the sequences can be selected to provide for restriction sites that are blunt-ended or have complementary overlaps.

The various manipulations for preparing the constructs hereof can be carried out in vitro and in particular embodiments the construct is introduced into vectors for cloning and expression in an appropriate host using standard transformation or transfection methods. Thus, after each manipulation, the resulting construct from joining of the DNA sequences is cloned, the vector isolated, and the sequence screened to ensure that the sequence encodes the desired transgene and expression control sequences. The sequence can be screened by restriction analysis, sequencing, or the like as desired.

Vectors of the embodiments presented herein may further employ eukaryotic promoters as is known in the art. Also, the vectors may contain a selectable marker, if for no other reason, to facilitate their manipulation in vitro. In other embodiments, the transgene can be expressed from mRNA in vitro transcribed from a DNA template.

In an exemplary nucleic acid construct (polynucleotide) employed according to the embodiments, the promoter is operably linked to the nucleic acid sequence encoding a transgene of the embodiments, i.e., they are positioned so as to promote transcription of the messenger RNA from the DNA encoding the single-agent construct. The promoter can be of genomic origin or synthetically generated. Alternatively, a number of well-known viral promoters are also suitable.

For expression of a construct of the present disclosure in NK cells or an NK cell line, the naturally occurring or endogenous transcriptional initiation region of the nucleic acid sequence encoding the transgene can be used to generate the desired expression in the target host. Alternatively, an exogenous transcriptional initiation region can be used that allows for constitutive or inducible expression, wherein expression can be controlled depending upon the target host, the level of expression desired, the nature of the target host, and the like.

Likewise, in some cases, a leader and/or signal sequence added to the N-terminus specific for human protein expression directing the construct to be encoded by the transgene to the cell surface may be used. In at least one embodiment, the signal is SEQ ID NO: 6.

Isolated nucleic acid segments and expression cassettes incorporating the DNA sequences of the constructs of the present disclosure are also provided. One of skill in the art will appreciate that such constructs may be employed with known gene modification techniques, including viral transduction, mRNA or DNA electroporation, and other viral and non-viral transduction and transfection techniques, to achieve engineered NK cells and/or an engineered NK cell line that expresses the constructs described herein.

Methods of making and/or expanding the engineered NK cells of the present disclosure are also provided. In at least one embodiment, a polynucleotide that encodes a construct provided herein can be introduced into a subject's own cells (or into cells from a different donor subject) using conventional transfection and/or transducing methods, either in a suitable vector or vector-free. Methods of stably transducing or transfecting NK cells by electroporation or otherwise are known in the art. In further aspects, the present constructs can be introduced into cells using a transposon-based system to mediate integration of the construct into genomic DNA of the cells, a non-viral vector, or a viral vector (e.g., a retroviral vector, adenoviral vector, adeno-associated viral vector, or lentiviral vector). Furthermore, in at least one embodiment, the CAR may be modified to facilitate uptake by the NK cells and, thus, expression of the construct-derived fusion protein in NK cells.

Sources of native NK cells may include both allogeneic and autologous sources. In some cases, NK cells may be differentiated from stem cells or induced pluripotent stem cells (iPSCs). For example, a construct as described herein can be expressed in stem cells or iPSCs, which can then be differentiated into NK cells using methods known to one skilled in the relevant arts. Thus, a cell for engineering according to the embodiments hereof can be isolated from umbilical cord blood, peripheral blood, human embryonic stem cells, or iPSCs.

In other embodiments, the NK cells are primary human NK cells, such as NK cells derived from human peripheral blood mononuclear cells or umbilical cord blood. In at least one exemplary embodiment, the engineered NK cells may be produced from recurrent and primary patient-derived cells pursuant to methods known in the art. Alternatively, the engineered NK cell(s) and/or engineered NK cell line expressing the constructs of the present disclosure can be produced from a standardized cell population to provide a homogenous NK cell population that can be grown to clinical scale.

The NK cells, stem cells, or iPSCs modified to express a construct described herein may be formulated into a pharmaceutical composition along with a "carrier" for delivery to a subject having a condition at least partially characterized by cells that can be targets of NK cytotoxicity (e.g., adenosine overexpressing disease state). As used herein, "carrier" includes any solvent, dispersion medium, diluent, antibacterial, coating, vehicle, and/or antifungal agent, isotonic agent, absorption delaying agent, buffer, carrier solution, suspension, colloid, and the like. The use of such media and/or agents is well known in the art. Except insofar as any conventional media or agent is incompatible with the active ingredient, its use in the pharmaceutical compositions hereof is contemplated. Supplementary active ingredients can also be incorporated into the compositions.

Furthermore, the pharmaceutical composition of the present disclosure (e.g., comprising a engineered cells expressing a construct hereof can be used alone or in combination with other well-established agents useful for treating cancer and/or solid tumor cancers. In at least one exemplary embodiment, one or more pharmaceutical compositions of the present disclosure may be administered to a single patient; for example, a first composition (or active ingredient) comprising engineered cells expressing a first construct of the present disclosure that is CD73-specific, a second composition (or active ingredient) comprising engineered cells expressing a second construct of the present disclosure that is CD39-specific, a third composition (or active ingredient) comprising engineered cells expressing a third construct of the present disclosure that is CD38-specific and further encodes cytokines, etc. It will be appreciated that any combination of the construct embodiments described herein may be utilized in formulating the pharmaceutical compositions hereof to achieve a desired effect.

Whether the composition itself comprises a combination of active ingredients or it is delivered alone or in combination with other agents or therapies, the pharmaceutical compositions hereof can be delivered via various routes and to various sites in a mammal, preferably a human, body to achieve a particular effect. One skilled in the art will recognize that, although more than one route can be used for administration, a particular route can provide a more immediate and/or more effective reaction than other routes. For example, intratumoral delivery may be used for the treatment of a solid tumor cancer (and may be advantageous in terms of minimizing off-target effects). Local or systemic delivery can be accomplished by administering the pharmaceutical composition into body cavities, infusion, or by parenteral introduction.

The pharmaceutical compositions may be formulated in a variety of forms adapted to a preferred route of administration. Accordingly, a composition can be administered via known routes including, without limitation, parenteral (e.g., intradermal, subcutaneous, intravenous, transcutaneous, intramuscular, intraperitoneal, etc.) or topical (e.g., intratracheal, intrapulmonary, etc.). A composition can also be administered via a sustained or delayed release.

A formulation may be conveniently presented in unit dosage form and may be prepared by methods well known in the art of pharmacy. Methods of preparing a composition with a pharmaceutically acceptable carrier include the step of bringing NK cells (and/or stem cells or iPSCs) modified to express a construct of the present disclosure into association with a carrier that constitutes one or more accessory ingredients. In general, a formulation may be prepared by uniformly and/or intimately bringing the engineered cells into association with, for example, a liquid carrier.

A pharmaceutical composition that includes NK cells (and/or stem cells or iPSCs) modified to express a construct hereof may be provided in any suitable form including but not limited to a solution, a suspension, an emulsion, a spray, an aerosol, or any form of mixture. The composition may be delivered in formulation with any pharmaceutically acceptable excipient, carrier, or vehicle. The effective amount of NK cells (and/or stem cells or iPSCs) modified to express a construct hereof that is administered to a subject can vary depending on various dosing factors discussed herein.

In some embodiments, the method can include administering a therapeutically effective amount of engineered cells modified to express a construct of the present disclosure to provide a dose of, for example, at or greater than about $10^9$ cells/subject, or from about $10^5$ cells/kg to about $10^{10}$ cells/kg to the subject, although in some embodiments the methods may be performed by administering an amount of engineered cells in a dose outside these ranges.

In some embodiments, the pharmaceutical composition that includes engineered cells modified to express a construct hereof may be administered, for example, from a single dose to multiple doses per week, although in some embodiments the method can be performed by administering the pharmaceutical composition at a frequency outside this range.

In any event, the amount of engineered cells administered should take into account the route of administration and should be such that a sufficient number of the engineered cells will be introduced so as to achieve the desired therapeutic response. Generally, the pharmaceutical composition is administered to a subject in an amount, and in a dosing regimen effective to treat the symptoms or clinical signs of the condition, which may include (without limitation) reducing, limiting the progression of, ameliorating, or resolving the same (to any extent).

The constructs, engineered cells and NK cell lines of the present disclosure may be used in many applications including, without limitation, treating a subject having an adenosine overexpressing cancer or other disease state through reducing the size of a tumor or other targeted cell or preventing the growth or re-growth of a tumor or other cancerous or malignant cells in treated subjects. Accordingly, embodiments of a method 1500 for treating a subject having an adenosine overexpressing cancer or related disease state are also provided.

Figure 15:
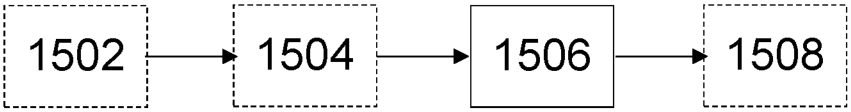
FIG. 15 shows a flow chart representative of a method of treating a subject using at least one embodiment of a pharmaceutical composition of the present disclosure.

Now referring to FIG. 15, the method 1500 may comprise a step 1506 of administering (or having administered) to a subject a therapeutically effective amount of a pharmaceutical composition as described herein. For example, the pharmaceutical composition may comprise a first population of engineered cells (as described herein) that express 1) a first polynucleotide construct that encodes at least an antigen binding domain (e.g., CD73 and, optionally, scFv) or a fragment thereof, and 2) stimulatory or costimulatory domains of a NK cell. As described herein, the antigen binding domain may be specific for an adenosine-producing or an adenosine-intermediary producing cell surface protein of a target cell and the stimulatory or costimulatory domains may comprise one or more domains involved in promoting cytotoxic or cytolytic activity of the engineered cell upon activation by the antigen binding domain binding the target cell. The target cell may comprise a T regulatory cell, a cancer cell, or a malignant cell in a TME, for example.

The administration 1506 step may be performed using any of the administration techniques heretofore described including, without limitation, intravenously, intratumorally (locally), parenterally, or via infusion (systematically).

Optionally, the method 1500 may also comprise steps of preparing the pharmaceutical composition for the subject. For example, optional step 1502 may comprise withdrawing, or having withdrawn, a sample, such sample comprising stem cells, blood cells, or iPSCs. Such withdrawn cells are thereafter isolated from the sample (i.e. in the case of a sample comprising a peripheral blood draw, one or more NK cells are isolated) and, if needed or desired, expanded. The sample may be obtained from the subject (e.g., an autologous cancer immunotherapy) and adoptive cell therapy is performed therewith. Alternatively, the sample may be provided from a donor separate from the subject (e.g., an allogeneic therapy). In at least one embodiment, the isolation, genetic modification, and/or any expansion steps are performed in vitro.

The method 1500 may also comprise optional step 1504 comprising transducing or transfecting the isolated cells are with an expression vector containing a construct of the present disclosure. For example, and without limitation, the CD73 scFv-FcγRIIIa construct may be employed. At step 1504, a population of engineered cells are achieved that express the desired construct. Such population of engineered cells may then be administered to the subject at step 1506 as previously described. In at least one embodiment, such administration comprises adoptive cell therapy. In yet another embodiment, multiple populations of engineered cells may be employed in one or more pharmaceutical compositions that are administered to the subject at step 1506. For example, and without limitation, a first population of engineered cells may express a first construct engineered such that the cells are CD73-specific, whereas a second population of engineered cells may express a second construct engineered such that the cells are CD39-specific. It will be appreciated that any number of combinations of the construct embodiments of the present disclosure may be employed.

Furthermore, it is contemplated that method 1500 may be combined with (or include) the administration of additional therapies now known or hereafter developed for the treatment of cancer, solid tumors, and/or related to ameliorating or eliminating symptoms or side-effects associated with such therapies (optional step 1508).

In at least one embodiment of such a method, a construct of the present disclosure is introduced into an isolated NK cell of the subject and, thereafter, the transformed NK cell is reintroduced into the subject, thereby effecting anti-tumor and/or anti-cancer responses to reduce or eliminate the condition in the subject. Suitable NK cells that can be used are addressed above and include, without limitation, blood-derived NK cells. Even non-NK cells as set forth herein may be employed. As is well known to one of ordinary skill in the art, various methods are readily available for isolating these cells from a subject, such as leukapheresis.

While various embodiments of constructs, engineered cells and cell lines, pharmaceutical compositions, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or too limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

EXAMPLES

The following examples illustrate certain specific embodiments of the present disclosure and are not meant to limit the scope of the invention in any way.

Example 1

Human Solid Tumors are $CD73^+$

Figure 2:
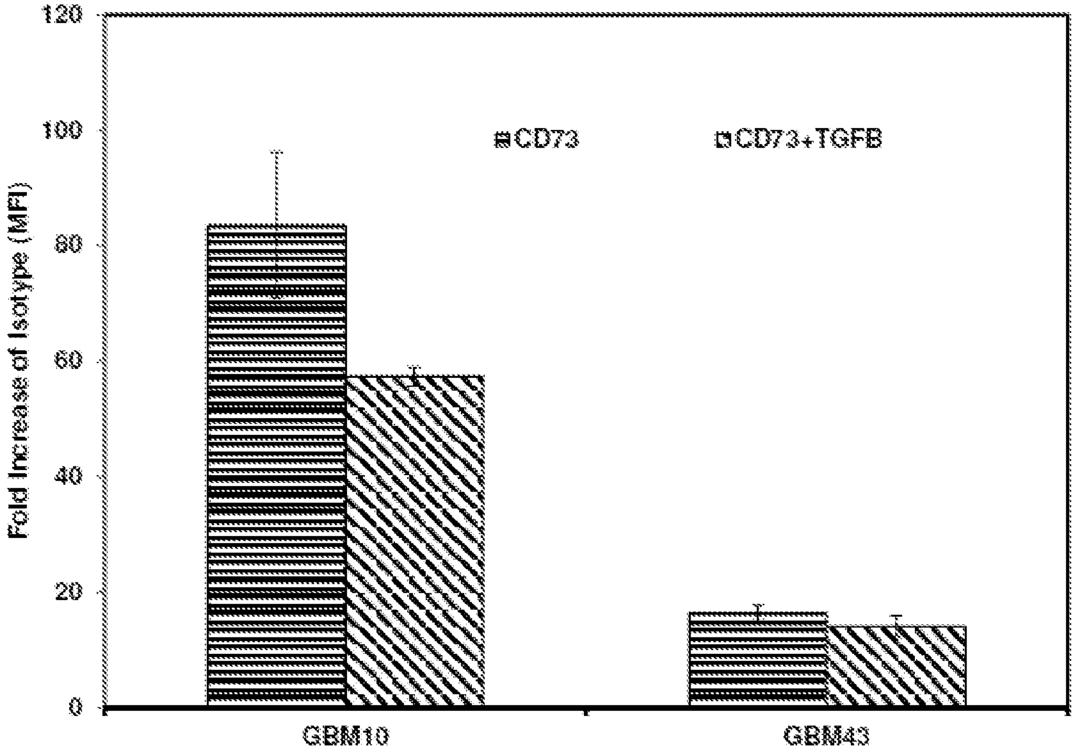
FIG. 2 is a graphical depiction of the expression of CD73 on glioblastoma (GBM), with recurrent (GBM10) and primary (GBM43) patient-derived cells expressing significant CD73 in the presence or absence of TGF-β.

It has been established that a CD73 blockade enhances immunotherapy with NK cells. CD73 is highly expressed on many human solid tumors, including A549 (lung carcinoma), PC3 (prostate cancer), GBM10/43 (glioblastoma ("GBM")). FIG. 2 shows data related to CD73 expression of glioblastoma cells, with recurrent (GBM10) and primary (GBM43) patient-derived cells expressing significant CD73 in the presence or absence of TGF-β. Native NK cells do not express CD73, thus making it a strong candidate for localizing target cells.

Example 2

Construct for Engineering NK Cells

Figure 3:
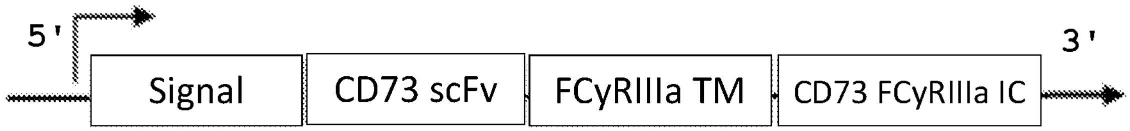
FIG. 3 is a schematic of the components of a genetic construct according to at least one embodiment of the present disclosure.

A genetic construct incorporating CD73 scFv was synthesized using a vector shown in FIG. 3 having the following components in frame from 5' end to 3' end: a leader sequence, the anti-CD73 scFv sequence, the truncated extracellular domain of FCyRIIIa (AA 189-208) the transmembrane domain of FCyRIIIa, and the intracellular domain of FCyRIIIa. The sequence encoding the construct (CD73.FcγRIIIa) was assembled in a cloning vector under the T7 promoter to allow for linearization and transcription. The cDNA was subcloned by PCR into a pcDNA3.1(+) plasmid allowing T7-dependent mRNA synthesis.

Figure 4B:
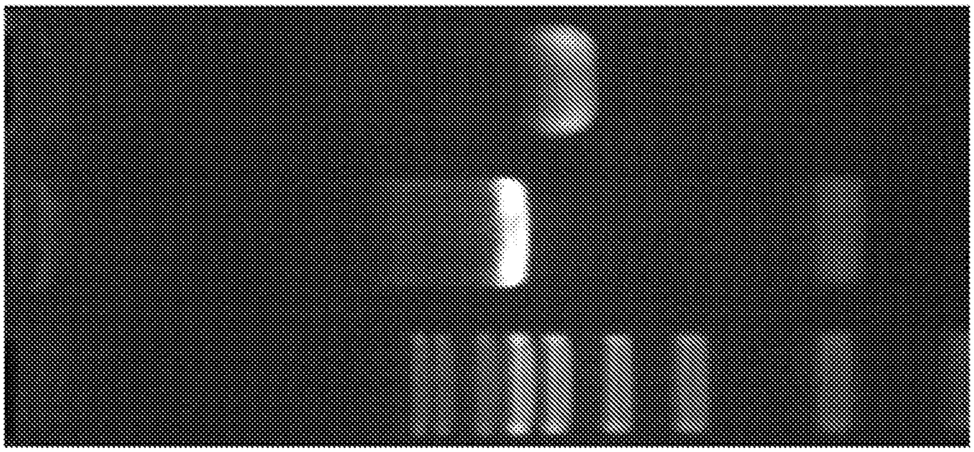
FIG. 4B shows a DNA gel showing the correct band corresponding to fully-synthesized vector encoding the target gene.
Figure 4A:
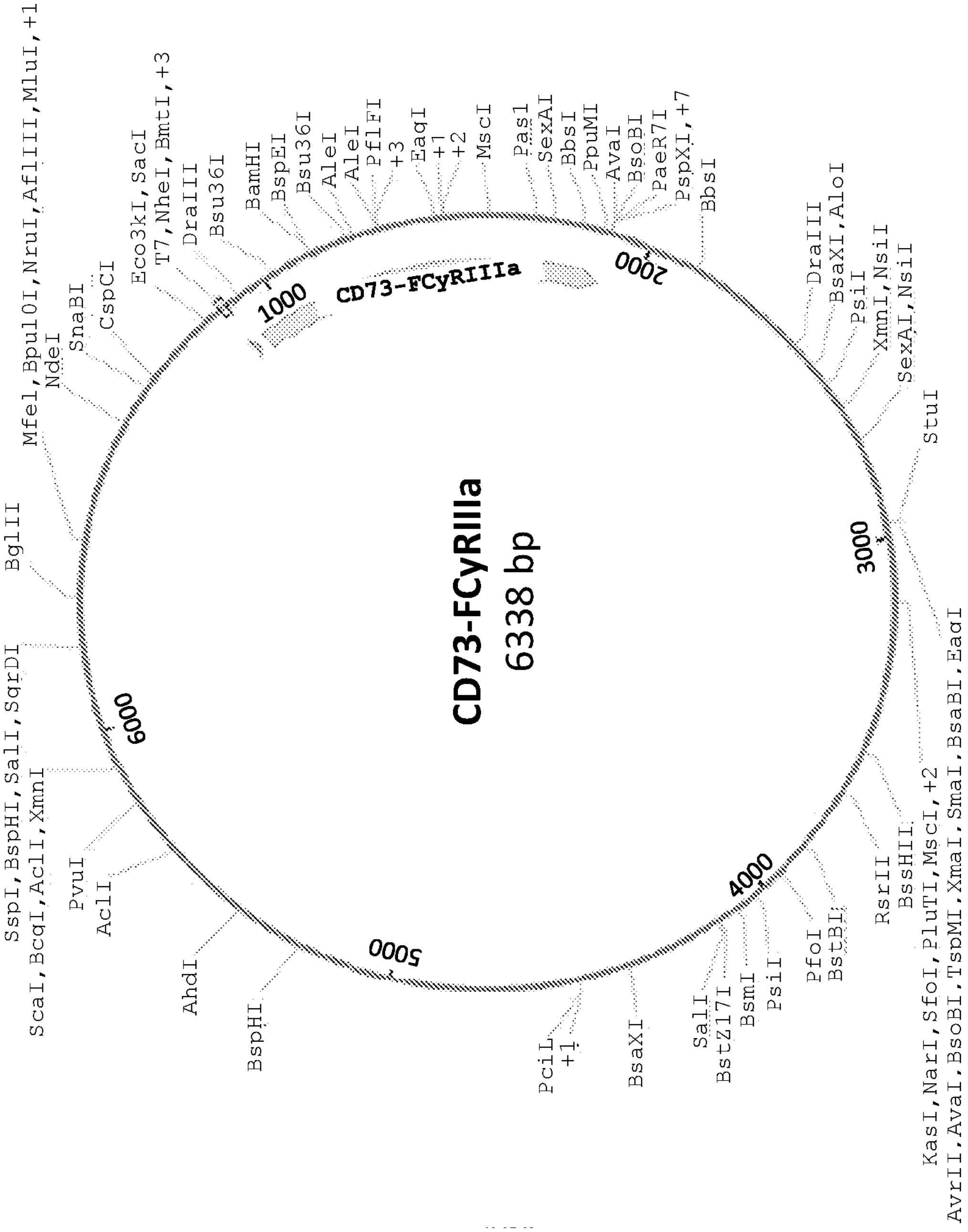
FIG. 4A shows a depiction of a sequence of a pcDNA3.1 (+) plasmid encoding CD73-FCγRIIIa. CAR of the present disclosure and DNA gel showing fully-synthesized vector encoding at least one embodiment of the construct design.

The overall plasmid contains restriction sites MfeI, SapI, BsiWI and AscI for linearization. The corresponding DNA sequence of the scFv portion was codon-optimized for optimal expression in human cells. The FCyRIIIa portions were derived from the sequence of human low affinity immunoglobulin gamma Fc region receptor III-A, codon-optimized and synthesized within the gene construct as described. FIG. 4A depicts a sequence of the synthesized construct CD73.FcγRIIIa.CAR expressed in a pcDNA3.1(+) vector, with FIG. 4B validating the construct was successfully synthesized and transcribed into mRNA. Indeed, the DNA gel of FIG. 4B supports that the fully-synthesized vector encoded the target gene as desired.

Further, to assess gene persistence, a transduction protocol was developed by synthesizing the transgene CD73.NK within a lentiviral vector (EF1α promoter). The results established efficient transduction in the presence of dextran hydrochloride with minimal toxicity.

Example 3

Expression of CD73 scFv-FcγRIIIa Fusion Protein on Engineered NK Cells

The gene construct of Example 2 was linearized and in vitro transcribed into mRNA using the HiScribe™ T7 ARCA mRNA Transcription kit and the restriction enzyme MfeI. mRNA electroporation was carried out using a Bio-Rad Gene Pulser Xcell® electroporator. Electroporation was performed with 5-20 μg RNA/100 μl electroporation buffer (Bio-Rad) containing ≤$1\times10^6$ NK cells immediately after isolation. Mock-transduced NK cells with mRNA not expressing the CAR construct were used as controls.

Following electroporation, cells were placed at 37° C. for 30 minutes in electroporation buffer prior to being transferred in culture media and expanded. Electroporated NK cells were further cultured in medium and used for functional analysis at least one day after mRNA transfection.

To detect expression of the gene construct, biotinylated human CD73 recombinant protein was bound to CD73.FcγRIIIa-NK cells. Using PE-labeled streptavidin, the expression of CD73 was detected through the measurement of PE by flow cytometry.

Before fluorescence-activated cell sorting staining, $1\times10^6$ cells were washed three times with FACS buffer (PBS containing 4% bovine serum albumin fraction V). Fluorescence was assessed using a BD Fortessa flow cytometer and all FACS data was analyzed with FlowJo software.

Figure 4C:
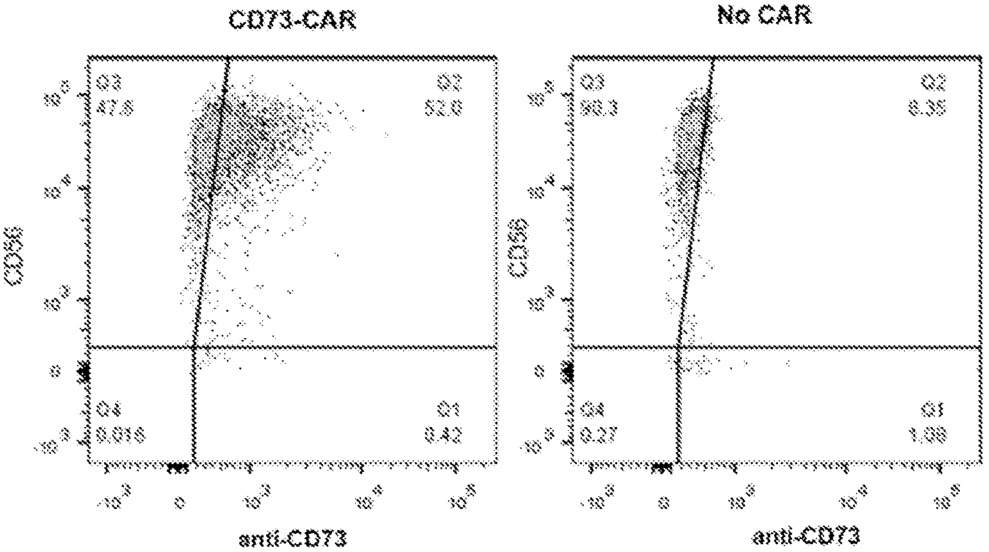
FIG. 4C shows a graphical representation of the expression of CD73 scFv on engineered NK cells of the present disclosure.

The ability of the construct of the present disclosure to be expressed in human NK cells following gene transfer by electroporation was verified (see FIG. 4C), supporting that human primary blood-derived NK cells can be engineered to successfully express the CD73.FcγRIIIa construct. Expression efficiencies at or above 40-50% were routinely obtained.

Figure 5:
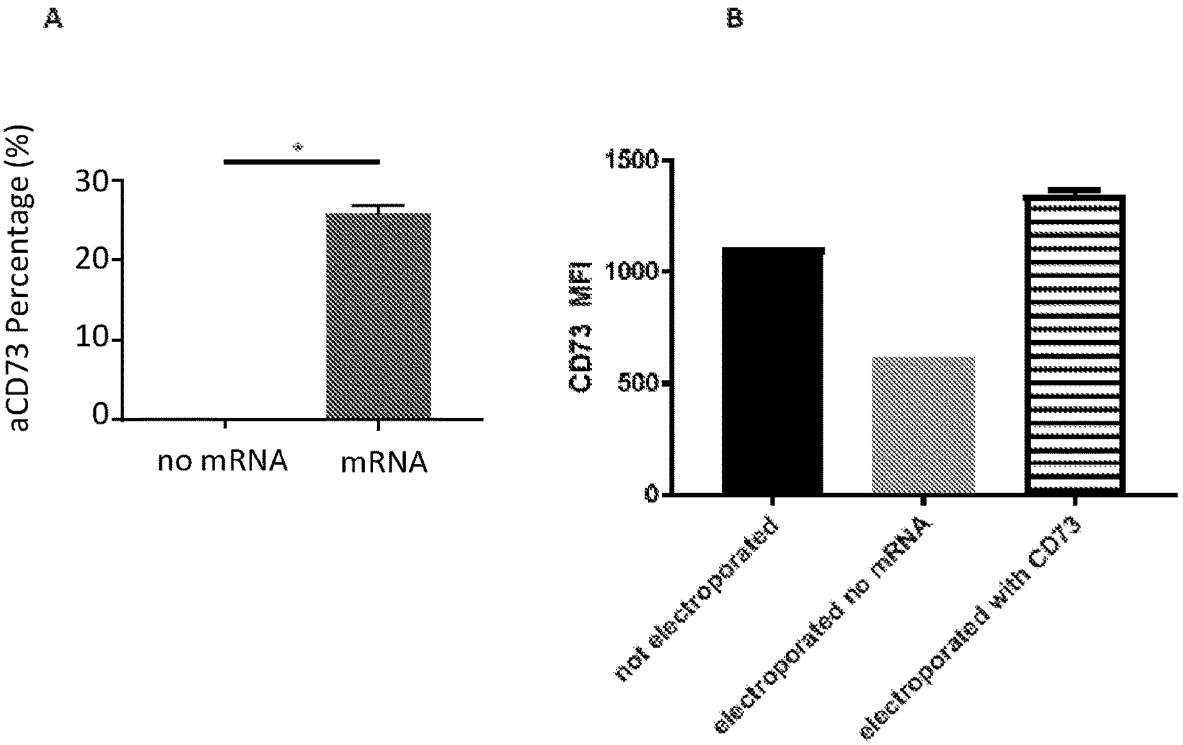
FIG. 5 is a graphical depiction of data evidencing that the human NK cells were engineered to successfully express the CD73.FcγRIIIa construct of the present disclosure, with subpart A evidencing that the expression was shown on a significant percentage of NK cells and subpart B evidencing a related MFI increase ($p<0.05$)

As seen in FIG. 5, a significant percentage of the engineered NK cells exhibited high expression of CD73 (subpart A). A significant MFI increase was also measured, further supporting these findings (subpart B).

Example 4

Verification of Engineered NK Cells Cytotoxicity Toward Solid Tumor Cells

The investigations heretofore described utilized primary blood-derived NK cells, isolated from peripheral blood of healthy volunteers via negative selection. To determine the functionality of our CD73-retargeted NK cells and their ability to kill tumor cells, CD73.FcγRIIIa-NK cells were stimulated for lysis of $CD73^+$ cells (U87MG a GBM cell line) and lung adenocarcinoma (LUAD) cells (A549) in vitro.

Cancer cells were grown in DMEM medium with 10% FBS and 2 mM glutamine for 72 hours before being used in the killing assay. Killing of cancer cells was detected via 7-AAD/CFSE staining.

Figure 1B:
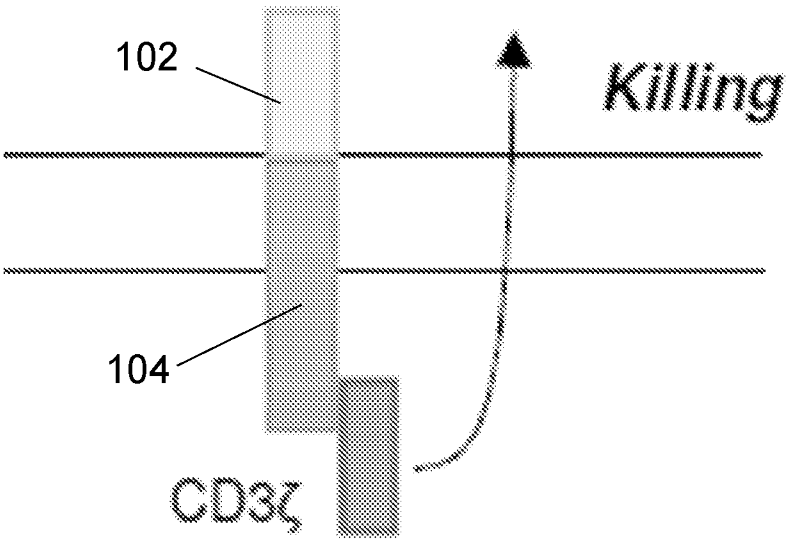
Figure 1C:
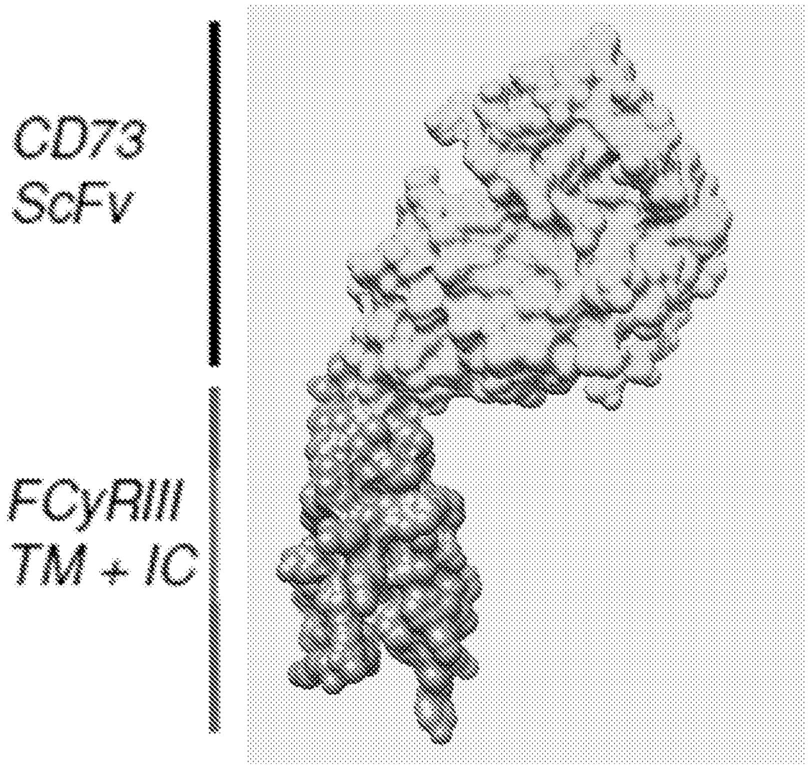

Accordingly, in operation, the CD73 engagement of the CD73-retargeted NK cells promotes signaling via transmembrane and intracellular domains of FcγRIIIa, resulting in activation of ITAM motifs on CD3ζ adaptor chains per the mechanism of FIG. 1B to trigger NK cell-mediated cytotoxicity against solid tumor targets. Local tumor lysis of $CD73^+$ GBM targets was aided by the present engineered NK cells in that it was accompanied by enhanced NK cell degranulation, cytokine production and chemokine expression in the vicinity of GBM tumor sites. In these ways, the engineered NK cells promoted NK cell infiltration.

Figure 6:
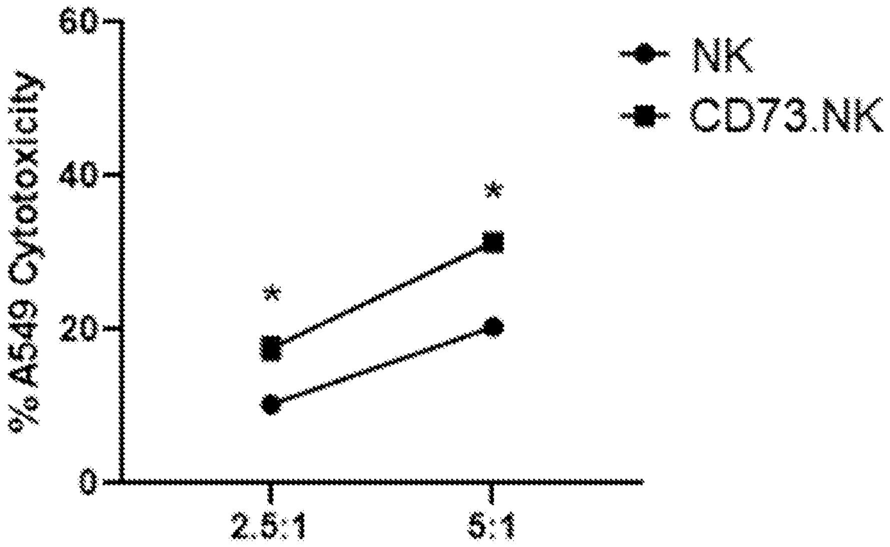
FIG. 6 shows data from an investigation of killing LUAD cells by CD73.FcγRIIIa as compared to human wild type NK cells (*$p<0.05$)

As noted above, the CD73.FcγRIIIa-NK cells were also tested against lung adenocarcinoma (LUAD) cells (A549). As compared to human wild-type or non-engineered NK cells, the CD73.FcγRIIIa-NK cells exhibited superior cytolysis against the cancer cells. For example, as shown in FIG. 6, the CD73.FcγRIIIa-NK cells killed more LUAD cells as compared to the wild type NK cells at E:T 2.5:1 and 5:1. This superior cytolysis was accompanied by enhanced NK cell degranulation. Because the efficiency of targeting an adenosine-producing or adenosine-intermediary-producing cell surface protein depends also on the extent of the enzymatic activity of such protein (here, CD73), the effects of the CD73 blockade are dependent on the level of CD73 activity in vitro, which is likely potentiated in vivo due to hypoxia.

Example 5

Figure 7:
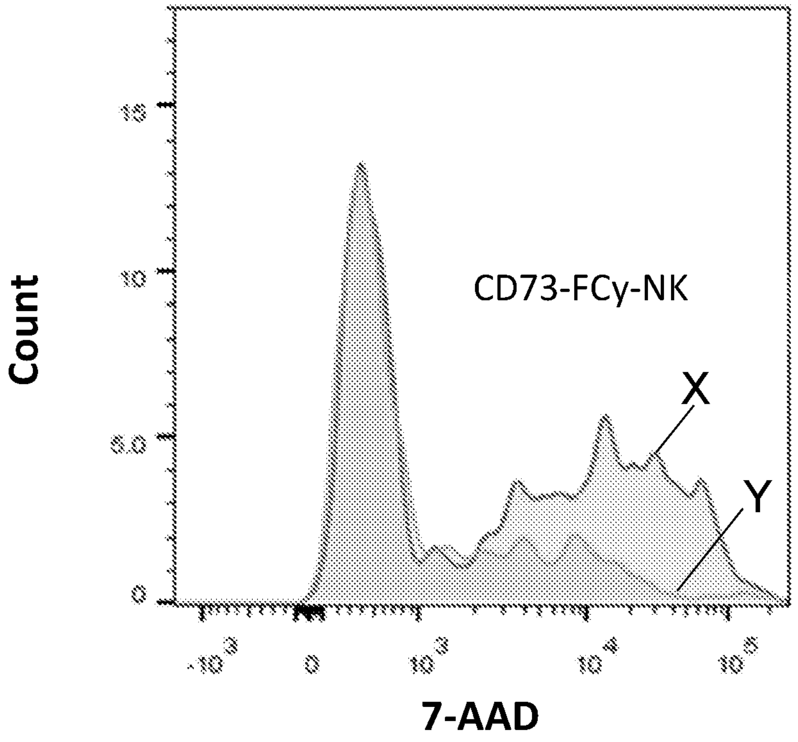
FIG. 7 illustrates graphical data representing the cytolysis rates of GBM cells (U87MG) of human NK cells engineered to express CD73.FcγRIIIa (labeled X) and non-CD73-targeting NK cells (labeled Y), supporting that the engineered NK cells (X) mediated more killing of GBM as compared to non-CD73-targeting NK cells (Y) (results consistent among donors; representative donor data shown)

Lentiviral Generated NK Cells Stably Expressed CD73scFv-FcγRIIIa Fusion Protein The transgene described above was also synthesized within a lentiviral vector to address any future manufacturability needs and verify that transduction can be achieved in the presence of retronectin. Human NK cells were engineered to express CD73.FcγRIIIa using the methods described herein and challenged to kill GBM cells (U87MG) at an E:T of 10:1. As shown in FIG. 7, CD73-redirected NK cells with the inventive NK-specific construct mediated effective cytolysis against GBM cells compared to human non-modified NK cells at E:T of 5:1. Enhanced killing by CD73-NK cells was also observed at E:T 5:1.

Figure 8:
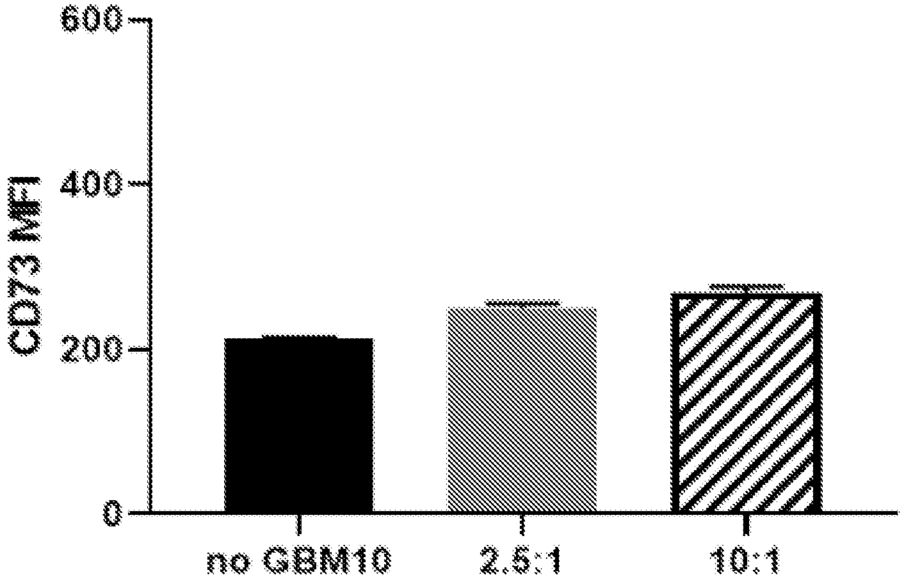
FIG. 8 shows graphical data regarding the expression of CD73 on NK cells interacting with GBM, and supports that NK CD73 expression only increased minimally after challenge with human GBM10 cells.

Though tumor-infiltrating NK cells can express more CD73 as compared to native blood NK cells, the present data supports that, in the presence of patient-derived recurrent GBM cells, NK CD73 expression is minimally altered in the presence of high-CD73-expressing cancer cells, such as GBM (see FIG. 8). Clinically, tumor-infiltrating NK cells similarly show expression of CD73 on a limited subset of NK cells. Accordingly, this data supports that infusing engineered NK cells can provide a competitive inhibition of their ability to express elevated CD73.

Example 6

CD73 scFv Blocks Enzymatic Activity of Cancer-Expressed CD73

To assess if CD73 scFv can effectively bind and block the enzymatic activity of CD73 expressed on lung cancer cells, the activity of CD73 was measured using malachite green, which reacts with free phosphate liberated from the generation of adenosine to release a complex that is measurable at 620-640 nm ($AMP \rightarrow ADO + P_i$). A genetic construct was generated, wherein the CD73 scFv was connected to a CAR with a protease-sensitive linker of SEQ ID NO: 4, flanked by a $(Gly\text{-}Ser)_3$ linker and a short Gly-Ser spacer (SEQ ID NO: 5). (As the focus of this investigation relates only to CD73 binding, stimulatory or costimulatory domains were not included in the construct.)

The CD73 scFv was cleaved from CAR-NK cells using urokinase plasminogen activator (uPa). The cleaved CD73 scFv was then isolated and incubated with $CD73^+$ cancer cells. Free phosphate levels where then assessed.

Figure 9:
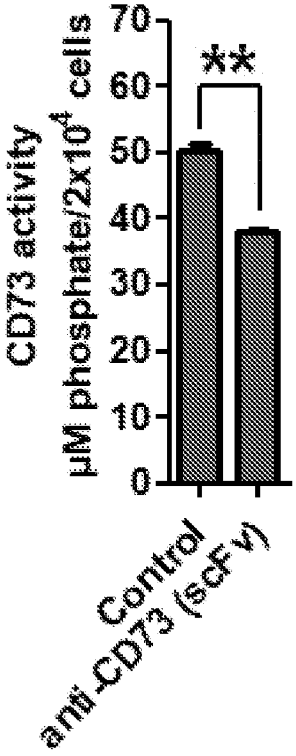
FIG. 9 shows a bar graph depicting malachite green assay results, with less free phosphate from cells blocked by the CD73 scFv of engineered NK cells according to at least one embodiment of the present disclosure (**$p<0.01$)

As shown in FIG. 9, significantly less free phosphate was generated by cancer cells in the samples with CD73 scFv as compared to those without, supporting that CD73 scFv successfully mediates a blockade of CD73 activity.

Example 7

Figure 10:
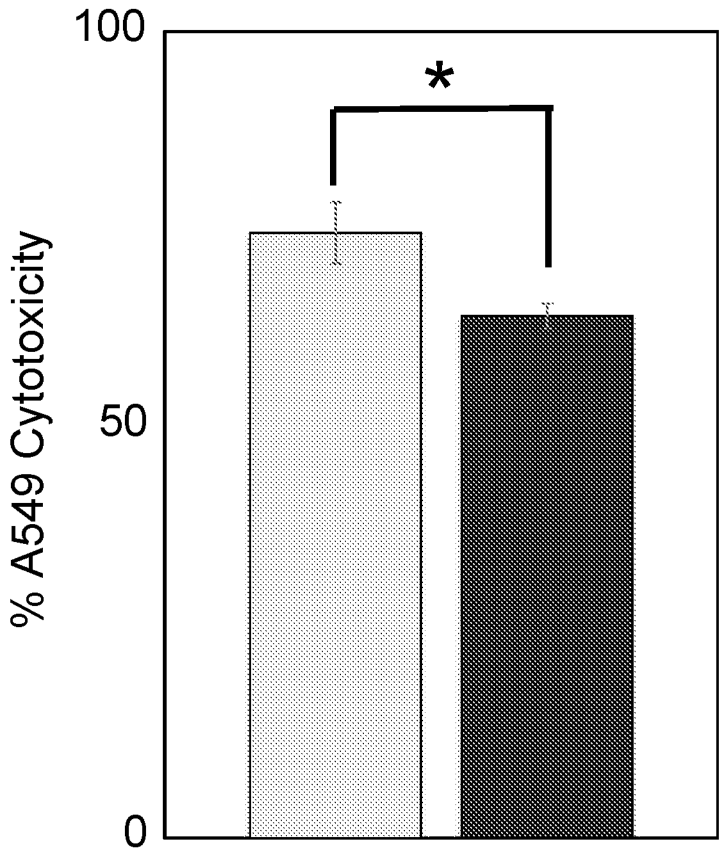
FIG. 10 shows a bar graph depicting the results of a study comparing the cytotoxicity of CD73.FcγRIIIa-NK cells (light bar; left) and a combination of wild-type NK cells+ anti-CD73 antibody (dark bar; right) with respect to killing A549 cells (*$p<0.05$)

CD73-Targeting CAR-NK Cells Promote Superior Cytotoxicity Against LUAD Cells Compared to Antibody Blockade Alone Further to Example 4, the CD73.FcγRIIIa-NK cells were also tested, in a killing assay as described in Example 4, against a combination of human wild-type NK cells and anti-CD73 antibodies with respect to their ability to kill lung adenocarcinoma (LUAD) cells (A549). As shown in FIG. 10, the CD73.FcγRIIIa-NK cells proved superior in killing the A549 cells, as measured by LDH. More significantly, single-agent multi-functional therapy was reported as clinically more beneficial for LUAD patients as compared to multi-agent injections, which aligns with the single agent approach described herein.

Example 8

Figure 11A:
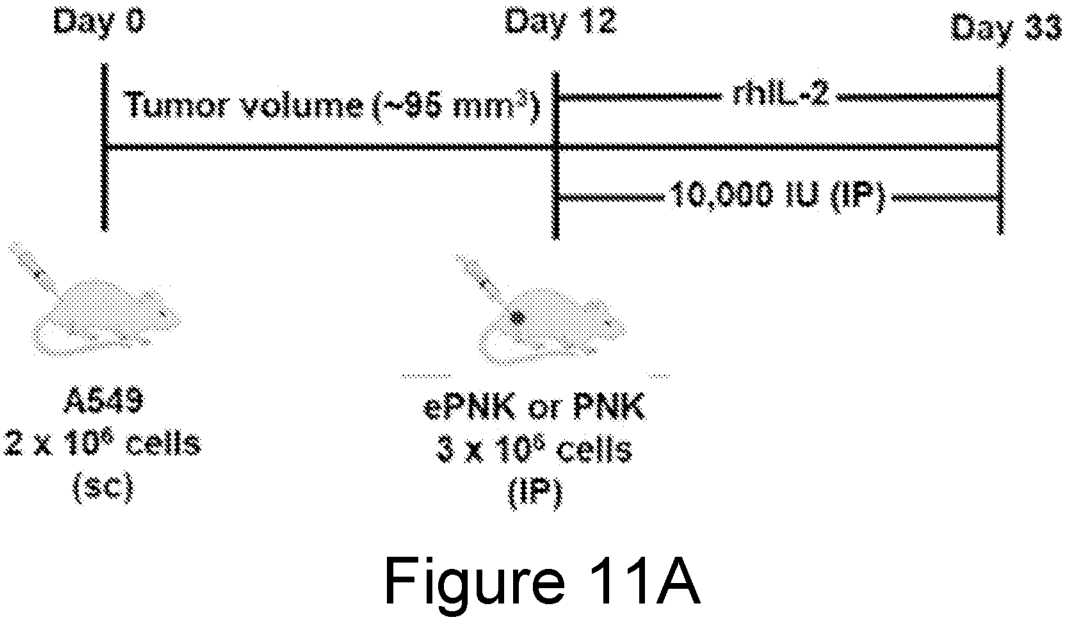
FIGS. 11A and 11B relate to the in vivo efficacy of CD73.FcγRIIIa-NK cells against LUAD xenografts, with FIG. 11A illustrating the adaptive transfer protocol, and FIG. 11B showing a graphical representation of the results supporting that tumors showed the greatest delay in progression for mice treated with CD73-targeting CD73.FcγRIIIa-NK cells (labeled CD73.NK) of the present disclosure (*$p<0.05$; difference from CD73.NK)
Figure 11B:
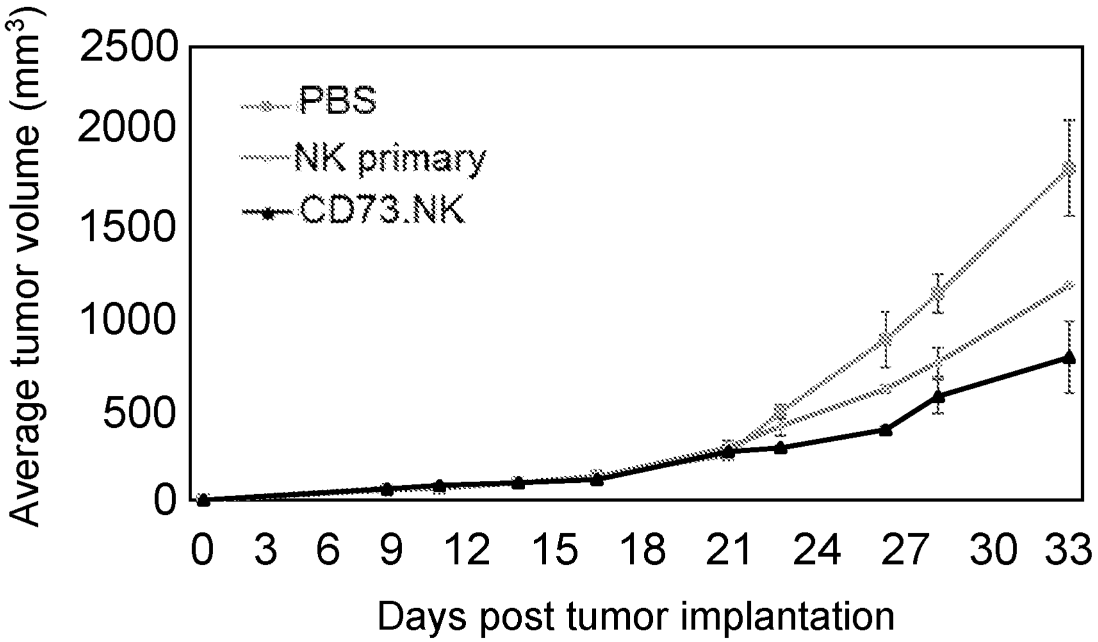

CD73-Targeting CAR-NK Cells Induce a Delay in Tumor Growth in CD73+ Lung Cancer Xenografts In Vivo When adoptively transferred into LUAD-bearing NSG mice pursuant to the protocol shown in FIG. 11A, CD73.FcγRIIIa-NK cells promoted significantly delayed LUAD growth compared to wild-type human NK cells (see FIG. 11B). NK cells were infused intraperitoneally (I.P.) at a concentration of $2\text{-}3\times10^6$ NK cells/mouse once weekly. These cells were administered alongside IL-2 therapy (>2000 U via single injection), infused I.P. every 2-3 days, to match the present investigators' previously published studies, although the use of IL-15 and other cytokines may also be beneficial. For example, and without limitation, in certain cases IL-15 may be superior to IL-2 in enhancing NK cell alloreactivity.

Example 9

Figure 12:
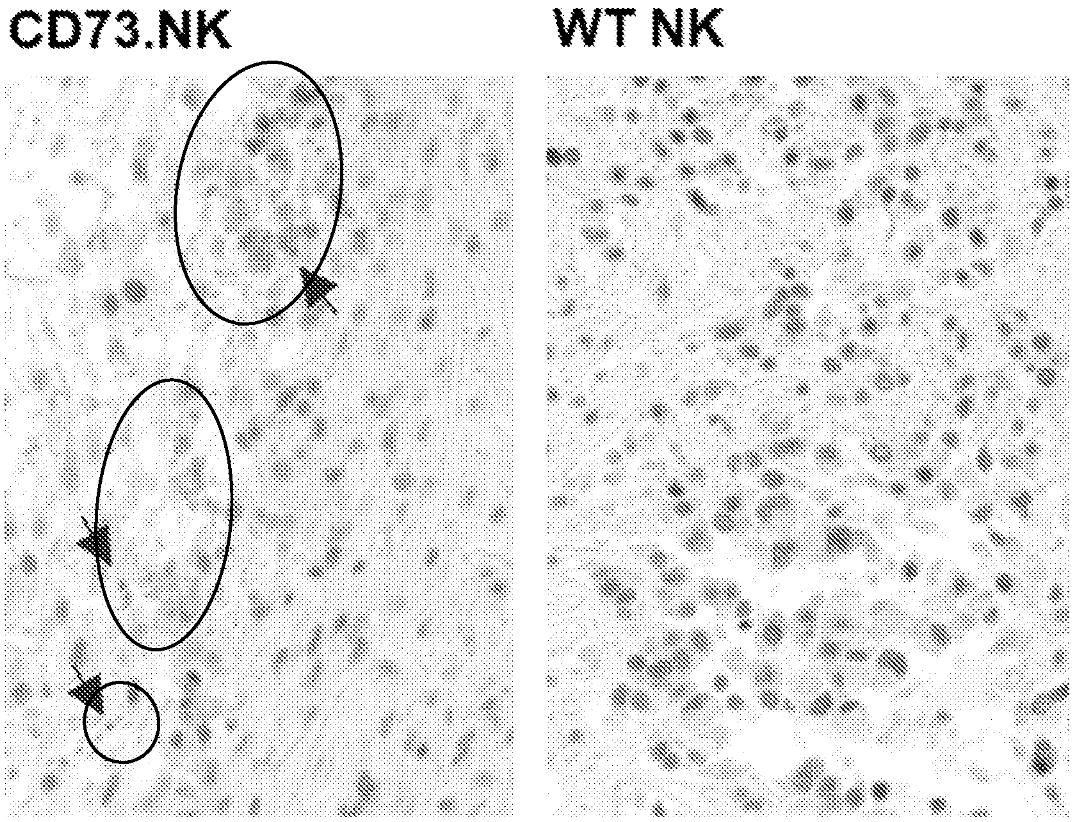
FIG. 12 shows IHC staining of $CD56^+$ CD73.FcγRIIIa-NK cells (labeled as CD73.NK) when adoptively transferred into LUAD-bearing NSG mice as compared to wild-type human NK cells (labeled WT NK)

CD73.FcγRIIIa-NK Cells are Able to More Deeply Home to LUAD Tumors In Vivo as Compared to Wild-Type Human NK Cells Lung tumors isolated from NSG mice following adaptive transfer therapy with CD73.FcγRIIIa-NK cells were analyzed by immunocytochemistry (IHC). Infiltration of $CD56^+$ CD73.FcγRIIIa-NK cells into LUAD tumors was detected in measurably higher amounts than that of wild-type human NK cells (see FIG. 12). These findings support that the engineered-NK cells of the present disclosure are more efficient than wild-type NK cells at homing to LUAD tumors in vivo.

Example 10

Figure 13:
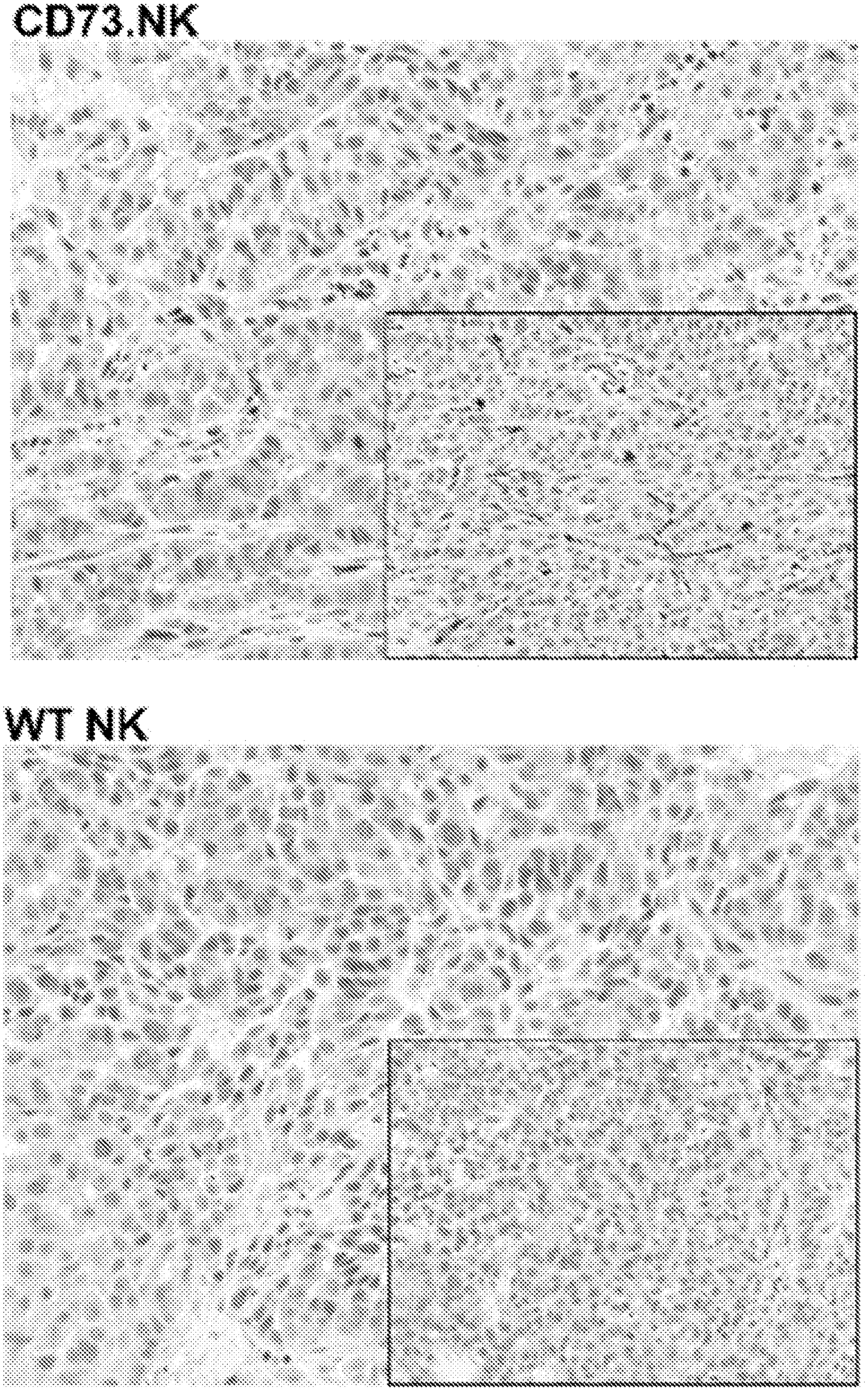
FIG. 13 shows IHC staining of granzyme B in A549 LUAD xenografts treated with CD73.FcγRIIIa-NK cells (labeled CD73.NK; top) and wild-type human NK cells (labeled WT NK; bottom), supporting that granzyme B is more expressed in A549 xenografts treated with CD73.FcγRIIIa-NK cells as compared to wild-type NK cells.

LUAD-Infiltrating CD73.FcγRIIIa-NK Cells Produce More Granzyme B In Vivo as Compared to Wild-Type Human NK Cells Lung cancer is typically associated with decreased expression of the cytotoxic NK granule protein granzyme B. In line with the observed deeper intratumoral infiltration of CD73.FcγRIIIa-NK cells into LUAD, IHC staining of LUAD tumors from NSG mice following adoptive transfer of CD73.FcγRIIIa-NK cells showed elevated expression of granzyme B (see FIG. 13). These finding correlate with a higher presence of NK cells and a higher release of cytotoxic granules in the tissues, thus supporting that the engineered-NK cells of the present disclosure produce increased amounts of granzyme B in vivo as compared to wild-type human NK cells.

Example 11

Figure 14:
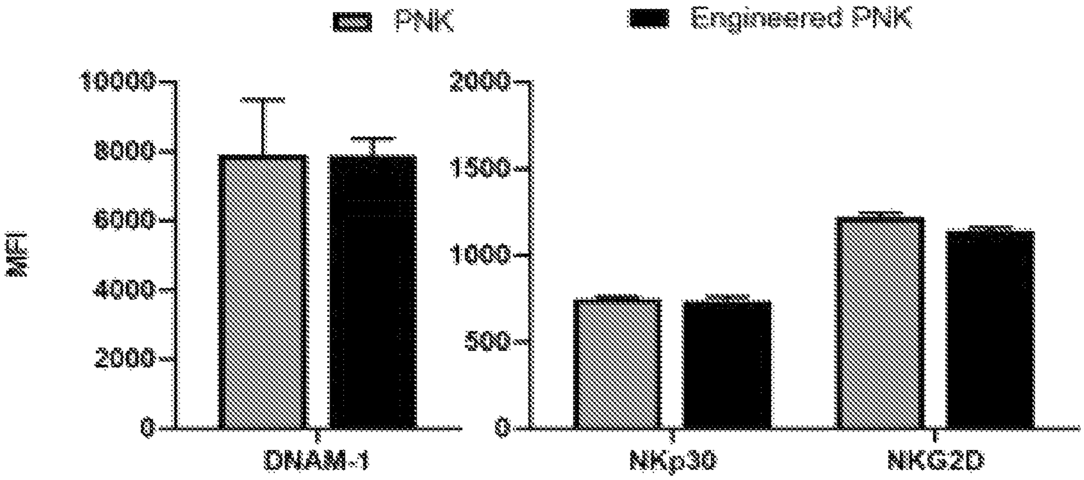
FIG. 14 shows a graph depicting marker expression of CD73.FcγRIIIa-NK cells isolated from the circulation of A549 NSG mice following adoptive transfer, with levels in the CD73.FcγRIIIa-NK cells (Engineered PNK) comparable to those of wild-type human NK cells (PNK)

Adoptively-Transferred CD73.FcγRIIIa-NK Cells Into Lung Cancer-Bearing Mice are Persistent and Express Activating NK Receptors Two weeks after adoptive transfer of CD73.FcγRIIIa-NK cells into LUAD-bearing mice, blood from mice was extracted and NK cells isolated via negative antibody selection to check for NK cell presence. CD73.FcγRIIIa-NK cells were present in the circulation of tumor-bearing mice, consistent with the administration of cytokine following adoptive transfer. As shown in FIG. 14, the recovered CD73.FcγRIIIa-NK cells expressed NK activating markers DNAM-1, NKG2D, and NKp30, similar to wild-type peripheral blood NK cells. As such, CD73.FcγRIIIa-NK cells exhibit sufficient persistence for adoptive-transfer applications.

The invention claimed is:

1. A polynucleotide construct comprising a first sequence operably linked to a second sequence, the first sequence encoding at least an antigen binding domain or fragment thereof that is specific for an adenosine-producing or an adenosine-intermediary-producing cell surface protein of a target cell, wherein first sequence encodes the antigen binding domain or fragment thereof having SEQ ID NO: 2, and the second sequence encoding one or more stimulatory or costimulatory domains of a natural killer (NK) cell for promoting cytotoxic or cytolytic activity upon activation; and wherein the polynucleotide construct comprises a sequence having at least 85% sequence identity to SEQ ID NO: 9.

2. The polynucleotide construct of claim 1, wherein the one or more stimulatory or costimulatory domains comprises a transmembrane domain, an intracellular domain, and at least a portion of an extracellular domain.

3. The polynucleotide construct of claim 2, wherein the one or more stimulatory or costimulatory domains are selected from a group consisting of FcγRIIIA, CD28, 4-1BB, OX40, FasL, TRAIL, NKG2D, DAP10, DAP12, NKp46, NKp44, NKp30, LFA-1, CD244, CD137, CD3ζ and a NKG2D-DAP10 receptor complex.

4. The polynucleotide construct of claim 1, wherein the one or more stimulatory or costimulatory domains are activated upon the antigen binding domain binding the target cell.

5. The polynucleotide construct of claim 1, wherein the antigen binding domain or fragment thereof is specific for CD73, and the target cell is a T regulatory cell, a cancer cell, or a malignant cell in a tumor microenvironment.

6. The polynucleotide construct of claim 1, wherein the one or more stimulatory or costimulatory domains comprise a Fcγ-signal molecule.

7. The polynucleotide construct of claim 6, wherein the one or more stimulatory or costimulatory domains comprise a transmembrane domain of FcγRIIIA, an intracellular domain of FcγRIIIA, and a truncated extracellular domain of FcγRIIIA.

8. The polynucleotide construct of claim 1, further comprising a third sequence that encodes a hinge domain, the third sequence operably linked to and positioned between the first sequence and the second sequence.

9. The polynucleotide construct of claim 1, wherein the first sequence is SEQ ID NO: 7.

10. The polynucleotide construct of claim 1, wherein the second sequence further comprises a nucleotide sequence that encodes CD3ζ.

11. An engineered cell or cell line that expresses a polynucleotide construct that encodes at least an antigen binding domain or a fragment thereof and one or more stimulatory or costimulatory domains of a natural killer (NK) cell, wherein the antigen binding domain or fragment thereof is specific for CD39 or CD157 of a target cell, and the one or more stimulatory or costimulatory domains promote cytotoxic or cytolytic activity of the engineered cell or cell line upon activation, wherein the one or more stimulatory or costimulatory domains comprises a Fc-signal molecule that comprises at least a transmembrane domain of FcγRIIIA and an intracellular domain of FcγRIIIA.

12. An engineered cell or cell line that expresses a polynucleotide construct that encodes at least an antigen binding domain or a fragment thereof and one or more stimulatory or costimulatory domains of a natural killer (NK) cell, wherein the antigen binding domain or fragment thereof is specific for CD39 or CD157 of a target cell, and the one or more stimulatory or costimulatory domains promote cytotoxic or cytolytic activity of the engineered cell or cell line upon activation, wherein the engineered cell is a NK cell and each NK cell is stem-cell derived.

13. The engineered cell or cell line of claim 11, wherein the one or more stimulatory or costimulatory domains comprises a transmembrane domain of FcγRIIIA, an intracellular domain of FcγRIIIA, and at least a partial extracellular domain of FcγRIIIA.

* * * * *

SEQUENCE LISTING

<160> NUMBER OF SEQ ID NOS: 9

<210> SEQ ID NO 1
<211> LENGTH: 20
<212> TYPE: PRT
<213> ORGANISM: Artificial Sequence
<220> FEATURE:
<223> OTHER INFORMATION: signal peptide

<400> SEQUENCE: 1

Met Glu Thr Asp Thr Leu Leu Leu Trp Val Leu Leu Leu Trp Val Pro
1               5                   10                  15

Gly Ser Thr Gly
20

<210> SEQ ID NO 2
<211> LENGTH: 242
<212> TYPE: PRT
<213> ORGANISM: Artificial Sequence
<220> FEATURE:
<223> OTHER INFORMATION: an engineered antigen binding domain specific for CD73 and including a scFv

<400> SEQUENCE: 2

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Tyr Ser Trp Val Arg Gln Ala Pro Gly Lys Gly Leu Glu Trp Val
35 40 45

Ser Ala Ile Ser Gly Ser Gly Gly Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Gly Tyr Gly Arg Val Asp Glu Trp Gly Arg Gly Thr Leu
100 105 110

Val Thr Val Ser Ser Gly Gly Gly Gly Ser Gly Gly Gly Gly Ser Gly
115 120 125

Gly Gly Gly Ser Gln Ser Val Leu Thr Gln Pro Pro Ser Ala Ser Gly
130 135 140

Thr Pro Gly Gln Arg Val Thr Ile Ser Cys Ser Gly Ser Leu Ser Asn
145 150 155 160

Ile Gly Arg Asn Pro Val Asn Trp Tyr Gln Gln Leu Pro Gly Thr Ala
165 170 175

Pro Lys Leu Leu Ile Tyr Leu Asp Asn Leu Arg Leu Ser Gly Val Pro
180 185 190

Asp Arg Phe Ser Gly Ser Lys Ser Gly Thr Ser Ala Ser Leu Ala Ile
195 200 205

Ser Gly Leu Gln Ser Glu Asp Glu Ala Asp Tyr Tyr Cys Ala Thr Trp
210 215 220

Asp Asp Ser His Pro Gly Trp Thr Phe Gly Gly Gly Thr Lys Leu Thr
225 230 235 240

Val Leu

<210> SEQ ID NO 3
<211> LENGTH: 65
<212> TYPE: PRT
<213> ORGANISM: Artificial Sequence
<220> FEATURE:
<223> OTHER INFORMATION: human FCyRIIIa stimulatory domain of a natural killer cell having a truncated extracellular domain

<400> SEQUENCE: 3

Ile Thr Gln Gly Leu Ala Val Ser Thr Ile Ser Ser Phe Phe Pro Pro
1 5 10 15

Gly Tyr Gln Val Ser Phe Cys Leu Val Met Val Leu Leu Phe Ala Val
20 25 30

```
Asp Thr Gly Leu Tyr Phe Ser Val Lys Thr Asn Ile Arg Ser Ser Thr
        35                  40                  45

Arg Asp Trp Lys Asp His Lys Phe Lys Trp Arg Lys Asp Pro Gln Asp
    50                  55                  60

Lys
65


<210> SEQ ID NO 4
<211> LENGTH: 8
<212> TYPE: PRT
<213> ORGANISM: Artificial Sequence
<220> FEATURE:
<223> OTHER INFORMATION: a protease-sensitive linker

<400> SEQUENCE: 4

Leu Ser Gly Arg Ser Asp Asn His
1               5


<210> SEQ ID NO 5
<211> LENGTH: 28
<212> TYPE: PRT
<213> ORGANISM: Artificial Sequence
<220> FEATURE:
<223> OTHER INFORMATION: a protease-sensitive linker flanked by a
      (Gly-Ser)3 linker and a short Gly-Ser spacer

<400> SEQUENCE: 5

Gly Gly Gly Gly Ser Gly Gly Gly Gly Ser Gly Gly Gly Gly Ser Leu
1               5                   10                  15

Ser Gly Arg Ser Asp Asn His Gly Ser Ser Gly Thr
            20                  25


<210> SEQ ID NO 6
<211> LENGTH: 60
<212> TYPE: DNA
<213> ORGANISM: Homo sapiens

<400> SEQUENCE: 6

atggaaccct ggcccctgct gctgctgttt agcctgtgct ctgctggact ggtgctgggc     60


<210> SEQ ID NO 7
<211> LENGTH: 726
<212> TYPE: DNA
<213> ORGANISM: Artificial Sequence
<220> FEATURE:
<223> OTHER INFORMATION: an engineered antigen binding domain specific
      for CD73 and including a scFv

<400> SEQUENCE: 7

gaggtgcagc tgctggaatc tggcgggggc ctggtgcagc caggaggctc cctgaggctg     60

tcttgcgcag caagcggctt cacctttagc tcctacgcct attcctgggt gagacaggca    120

cctggcaagg gcctggagtg ggtgtctgcc atctccggct ctggcggcag gacatactat    180

gccgacagcg tgaagggccg gttcaccatc tccagagata actctaagaa tacactgtac    240

ctgcagatga actccctgag ggcagaggac accgccgtgt actattgcgc aaggctggga    300

tatggaaggg tggatgagtg gggaaggggc accctggtga cagtgtctag cggaggagga    360

ggatctggag gaggaggaag cggcggagga ggcagccagt ccgtgctgac acagccacct    420

tctgccagcg gaacccctgg acagagggtg acaatctcct gttctggcag cctgtccaac    480

atcggccgca acccagtgaa ttggtaccag cagctgccag gaaccgcacc aaagctgctg    540

atctatctgg acaatctgcg gctgagcggc gtgcccgata gattttctgg cagcaagtcc    600
```

ggcacatctg ccagcctggc aatcagcggc ctgcagtccg aggacgaggc agattactat 660
tgtgccacct gggatgactc tcaccctggc tggactttcg ggggaggaac taaactgacc 720
gtgctg 726

<210> SEQ ID NO 8
<211> LENGTH: 195
<212> TYPE: DNA
<213> ORGANISM: Artificial Sequence
<220> FEATURE:
<223> OTHER INFORMATION: human FCyRIIIa stimulatory domain of a natural killer cell having a truncated extracellular domain

<400> SEQUENCE: 8
attacccagg gcctggcggt gagcaccatt agcagctttt ttccgccggg ctatcaggtg 60
agcttttgcc tggtgatggt gctgctgttt gcggtggata ccggcctgta ttttagcgtg 120
aaaaccaaca ttcgcagcag cacccgcgat tggaaagatc ataaatttaa atggcgcaaa 180
gatccgcagg ataaa 195

<210> SEQ ID NO 9
<211> LENGTH: 990
<212> TYPE: DNA
<213> ORGANISM: Artificial Sequence
<220> FEATURE:
<223> OTHER INFORMATION: an artificial construct having CD73 scFv fused with human FcyRIIIa having a truncated extracellular domain

<400> SEQUENCE: 9
aagcttgcca ccatgtggca gctgctgctg cctaccgctc tgctgctgct ggtctccgcc 60
gaagtccagc tgctggaaag tggggggggc ctggtccagc caggaggcag cctgaggctg 120
tcctgcgcag catctggctt cacctttagc tcctacgcct attcttgggt gagacaggca 180
ccaggcaagg gcctggagtg ggtgagcgcc atcagcggat ccggaggcag gacatactat 240
gccgactccg tgaagggccg gtttaccatc agcagagata actccaagaa tacactgtac 300
ctgcagatga actccctgag ggcagaggac accgccgtgt actattgcgc aaggctggga 360
tatggaaggg tggatgagtg ggaagggggc accctggtga cagtgtctag cggaggagga 420
ggatccggag gaggaggatc tggcggcggc ggctctcaga gcgtgctgac ccagccacct 480
tccgcctctg gaaccccagg ccagagggtg acaatcagct gttccggctc tctgagcaac 540
atcggccgca accctgtgaa ttggtaccag cagctgcctg gcaccgcccc aaagctgctg 600
atctatctgg acaatctgcg gctgtctggc gtgcctgata gattttccgg ctctaagagc 660
ggcacatccg cctctctggc catctctggc ctgcagagcg aggacgaggc cgattactat 720
tgcgcaacct gggacgatag ccacccagga tggacattcg gcggaggaac caagctgaca 780
gtgctgatca cccagggcct ggccgtgagc acaatctcct ctttctttcc acccggctac 840
caggtgtcct tctgtctggt catggtgctg ctgtttgccg tggacaccgg cctgtatttc 900
agcgtgaaga caaatatcag atcatcaaca agagattgga aagaccataa gttcaagtgg 960
cggaaggacc cccaggacaa gtgactcgag 990